United States Patent
Tajima

(10) Patent No.: US 9,271,693 B2
(45) Date of Patent: Mar. 1, 2016

(54) REGULATING UNIT AND RADIOGRAPHIC IMAGING SYSTEM

(71) Applicant: FUJIFILM Corporation, Tokyo (JP)

(72) Inventor: Takashi Tajima, Ashigarakami-gun (JP)

(73) Assignee: FUJIFILM CORPORATION, Tokyo (JP)

(*) Notice: Subject to any disclaimer, the term of this patent is extended or adjusted under 35 U.S.C. 154(b) by 200 days.

(21) Appl. No.: 14/010,320

(22) Filed: Aug. 26, 2013

(65) Prior Publication Data

US 2014/0056408 A1 Feb. 27, 2014

(30) Foreign Application Priority Data

Aug. 27, 2012 (JP) ................................ 2012-186349

(51) Int. Cl.
*A61B 6/00* (2006.01)
*G01T 1/20* (2006.01)

(52) U.S. Cl.
CPC ............... *A61B 6/542* (2013.01); *G01T 1/2018* (2013.01); *A61B 6/4283* (2013.01); *A61B 6/467* (2013.01); *A61B 6/469* (2013.01); *A61B 6/586* (2013.01)

(58) Field of Classification Search
CPC ........ A61B 6/467; A61B 6/469; A61B 6/542; A61B 6/545; A61B 6/548; A61B 6/586; A61B 6/1048; A61B 6/1071; A61B 6/1075; A61B 6/4233; A61B 6/4283; G01T 1/02; G01T 1/023; G01T 1/2018
See application file for complete search history.

(56) References Cited

U.S. PATENT DOCUMENTS

| | | | | |
|---|---|---|---|---|
| 4,400,823 A | * | 8/1983 | Haendle | 378/113 |
| 5,949,811 A | * | 9/1999 | Baba et al. | 378/108 |
| 7,313,224 B1 | * | 12/2007 | Saunders et al. | 378/108 |
| 7,317,783 B2 | * | 1/2008 | Dolgonos | 378/106 |
| 7,639,784 B2 | * | 12/2009 | Feda | 378/118 |
| 7,844,031 B2 | | 11/2010 | Newman et al. | |
| 8,085,901 B2 | | 12/2011 | Newman et al. | |
| 2008/0224047 A1 | * | 9/2008 | Nakayama | 250/354.1 |

FOREIGN PATENT DOCUMENTS

JP 2011-036398 A 2/2011

OTHER PUBLICATIONS

Japanese Office Action dated Sep. 2, 2015 with an English translation.

* cited by examiner

*Primary Examiner* — David J Makiya
*Assistant Examiner* — Julio M Duarte-Carvajalino
(74) *Attorney, Agent, or Firm* — McGinn IP Law Group

(57) ABSTRACT

An X-ray imaging system or radiographic imaging system includes a radiation generating apparatus and a radiographic imaging apparatus. An ionization chamber device is external to the radiographic imaging apparatus, for detecting a dose of the radiation transmitted through an object. Dose sensors are incorporated in the radiographic imaging apparatus, for detecting a dose of the radiation transmitted through the object. An exposure control unit is disposed with the radiation generating apparatus, for shutting off application of the radiation from the radiation generating apparatus according to a detection signal from the ionization chamber device or dose sensors. The ionization chamber device is communicably coupled with the radiation generating apparatus. An operating state of the ionization chamber device and dose sensors is acquired by monitoring, so failure of simultaneous inputting of their detection signals to the exposure control unit is prevented.

19 Claims, 17 Drawing Sheets

FIG.3A

```
                        70
X-RAY GENERATING APPARATUS
        AEC INFO

70a —   AEC     ⊙ ENABLE (ON)

○ DISABLE (OFF)

70b —   LOCAL AREA  ⊙ CHEST

○ ABDOMEN

| 1ST AEC INFO ||
|---|---|
| 1ST SWITCHING OPERATION | 1ST AREA SELECTION |
| ON | CHEST |

| 2ND AEC INFO ||
|---|---|
| 2ND SWITCHING OPERATION | 2ND AREA SELECTION |
| ON | CHEST |

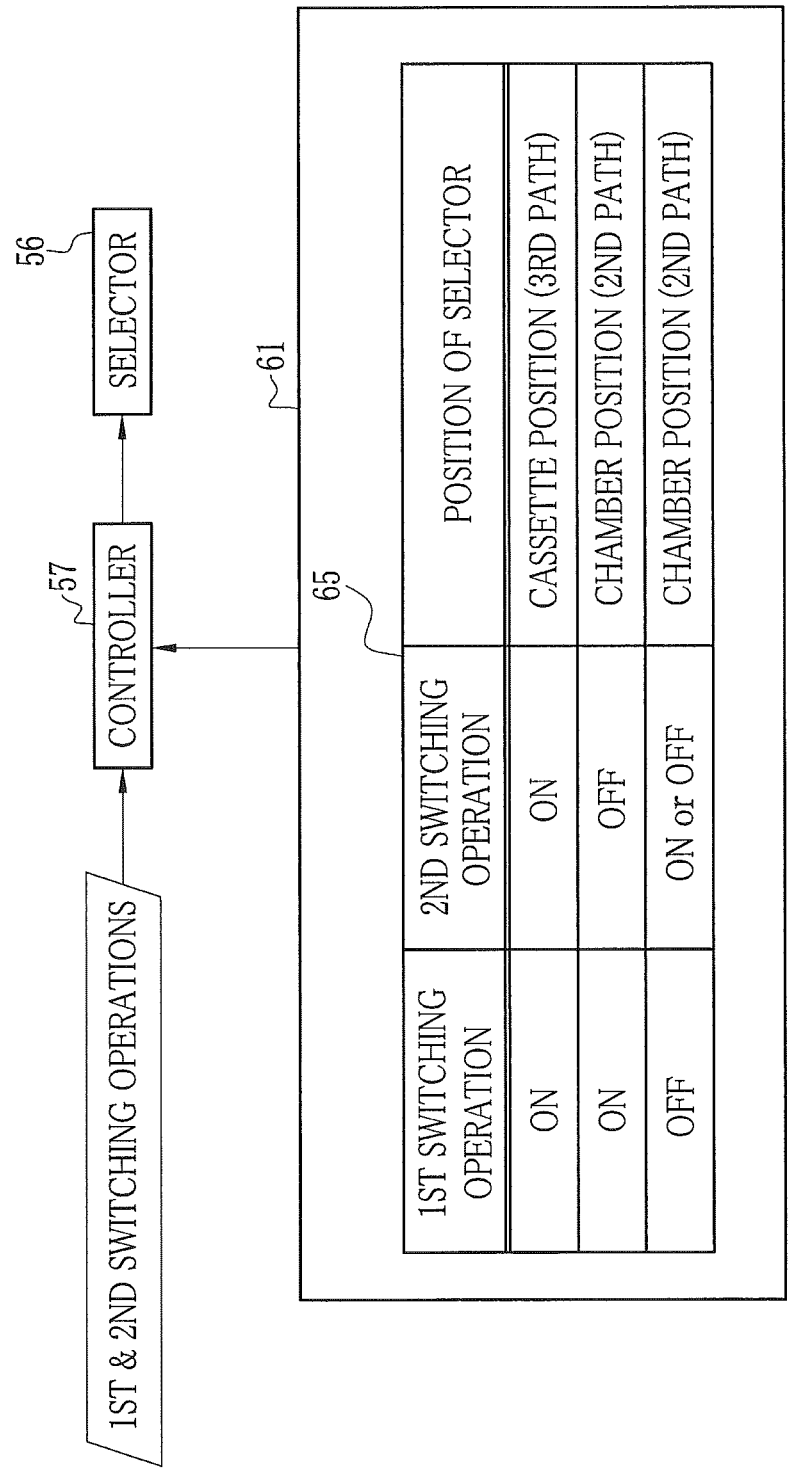

F I G . 14
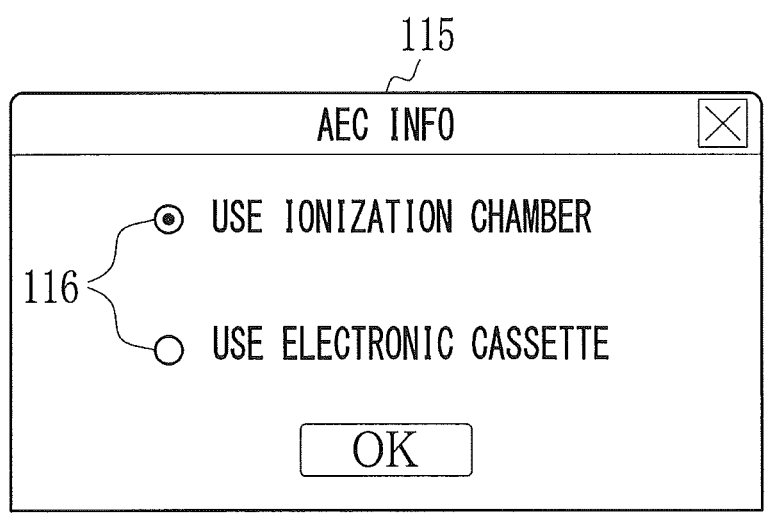

# REGULATING UNIT AND RADIOGRAPHIC IMAGING SYSTEM

BACKGROUND OF THE INVENTION

1. Field of the Invention

The present invention relates to a regulating unit and a radiographic imaging system. More particularly, the present invention relates to a regulating unit and a radiographic imaging system, in which a radiographic imaging unit has a function of automatic exposure control (AEC), and safety in the function can be maintained even in use of plural AEC signal output devices.

2. Description Related to the Prior Art

An X-ray imaging system as a radiographic imaging system is well-known in the field of medical imaging. The X-ray imaging system includes an X-ray generating apparatus as a radiation generating apparatus, and an X-ray imaging apparatus as a radiographic imaging apparatus. The X-ray imaging apparatus forms an X-ray image from X-rays transmitted through a body of a patient. The X-ray generating apparatus includes an X-ray source as a radiation source, a radiation source driver and a source switch. The X-ray source applies X-rays to an object. The radiation source driver controls the X-ray source. The source switch is operable to input a command signal for starting the irradiation to the radiation source driver. The X-ray imaging apparatus includes an electronic cassette or a radiographic imaging unit, and a computer terminal or console unit. The radiographic imaging unit detects the X-ray image from X-rays transmitted through the body having various body parts. The computer terminal drives and controls the radiographic imaging unit, and stores and displays the X-ray image.

An FPD device (flat panel detector device) has been recently utilized as the radiographic imaging panel as a newly developed device in place of an X-ray film or imaging plate (IP). The FPD device has an imaging area in which arrays of pixels are arranged for storing signal charge according to dose of incident X-rays. The FPD device stores signal charge per pixels, reads the stored signal charge through switching elements such as TFTs, and electrically detects the X-ray image by conversion of the signal charge into voltage signal in a signal processor.

Various medical service providers have wishes to use the radiographic imaging unit in combination with an X-ray film or imaging plate conventionally used widely even after introducing the radiographic imaging unit with the FPD device. A new type of the X-ray generating apparatus is marketed for compatibility with the radiographic imaging unit having the FPD device and the X-ray film or imaging plate. Also, an improvement of and an additional structure to the X-ray generating apparatus for the X-ray film or imaging plate have been suggested so that the X-ray generating apparatus for the X-ray film or imaging plate can become compatible with the radiographic imaging unit having the FPD device. The additional structure is disclosed in U.S. Pat. Nos. 7,844,031 and 8,085,901 (corresponding to JP-A 2011-502699).

In the FPD device, the resetting is periodically carried out for the purpose of removing charge from the pixels to minimize influence of electric noise of dark current in the X-ray image, as a difference from the X-ray film or imaging plate. It is necessary to synchronize a start of the storing after the resetting with a start of irradiation of X-rays from the X-ray source. U.S. Pat. Nos. 7,844,031 and 8,085,901 disclose a relay device (for connection and control) for connection of the source switch (operable switch), the radiation source driver (computer and the X-ray source), and the radiographic imaging unit (DR receiver panel) having the FPD device. The relay device sends a start signal or exposure signal to both of the radiation source driver and the radiographic imaging unit for synchronism. Thus, the radiographic imaging unit having the FPD device can be used with the X-ray generating apparatus for the X-ray film or imaging plate.

Also, U.S. Pat. Nos. 7,844,031 and 8,085,901 disclose a use of an external AEC signal output device (detection device), which is separate from the radiographic imaging unit, and shuts off irradiation of X-rays from the X-ray source when it is judged that the cumulative dose of the X-rays reaches a target dose. The external AEC signal output device is connected to the radiation source driver, and generates an AEC signal as a result of a detected dose of X-rays, or occurrence of the reach of the cumulative dose to the target dose. The radiation source driver shuts off the irradiation in response to the AEC signal.

There is a type of the radiographic imaging unit with the FPD device in which a built-in AEC signal output device (detection device) is incorporated. It is conceivable to combine the use of the built-in AEC signal output device with the use of the external AEC signal output device separate from the radiographic imaging unit as suggested in U.S. Pat. Nos. 7,844,031 and 8,085,901. However, there occurs a crosstalk between the AEC signals from the external AEC signal output device and the built-in AEC signal output device in the case of their simultaneous use. No AEC is carried out properly due to failure in operation of the radiation source driver, to expose an object to X-rays of a harmfully high dose.

U.S. Pat. Nos. 7,844,031 and 8,085,901 disclose synchronism between a start of the storing of the FPD device and a start of irradiation. However, no built-in AEC signal output device is included in the radiographic imaging unit with the FPD device. No solution is known for the problem with the combined use of the built-in AEC signal output device in the radiographic imaging unit with the FPD device and the external AEC signal output device separate from the radiographic imaging unit.

SUMMARY OF THE INVENTION

In view of the foregoing problems, an object of the present invention is to provide a regulating unit and a radiographic imaging system, in which a radiographic imaging panel has a function of automatic exposure control (AEC), and safety in the function can be maintained even in use of plural AEC signal output devices.

In order to achieve the above and other objects and advantages of this invention, a regulating unit for a radiographic imaging system is provided, the radiographic imaging system including a radiation generating apparatus, having a radiation source and a radiation source driver for driving the radiation source, for applying radiation to an object, a radiographic imaging apparatus, having a radiographic imaging panel, for detecting the radiation transmitted through the object, to create a radiation image, a first AEC signal output device, external to the radiographic imaging apparatus, for detecting a dose of the radiation transmitted through the object, to output a first AEC signal for automatic exposure control, a second AEC signal output device, incorporated in the radiographic imaging apparatus, for detecting a dose of the radiation transmitted through the object, to output a second AEC signal for automatic exposure control, and an exposure control unit, disposed with the radiation source driver, for shutting off application of the radiation from the radiation source according to the first or second AEC signal from the first or second AEC signal output device. The regulating unit includes an information acquisition device for acquiring at least one of first information of a first switching operation as to whether the first AEC signal output device should be used, second information of a second switching operation as to whether the second AEC signal output device should be used, and information of a connected state as to whether the first and second AEC signal output devices are connected to the radiation source driver. A controller prevents failure of simultaneous inputting of the first and second AEC signals to the exposure control unit according to the information acquired by the information acquisition device.

The information acquisition device acquires the first information of the first switching operation and the second information of the second switching operation. The controller sets a turn-on or turn-off state for the first and second AEC signal output devices according to the first and second information of the first and second switching operations.

If the first and second AEC signal output devices are in the turn-on state simultaneously, the controller carries out exclusive control of selecting one of the first and second AEC signal output devices.

The controller sets the turn-on or turn-off state of one of the first and second switching operations to the turn-off state by transmitting a command signal.

In another preferred embodiment, furthermore, a selector selectively switches a first signal path for inputting the first AEC signal from the first AEC signal output device to the exposure control unit and a second signal path for inputting the second AEC signal from the second AEC signal output device to the exposure control unit. The controller enables one of the first and second signal paths by use of the selector.

Furthermore, a memory stores priority information of a selected one of the first and second AEC signal output devices to which priority is given. The controller carries out the exclusive control according to the priority information.

The priority information is changeable by external operation.

If the first and second AEC signal output devices are in the turn-on state simultaneously, the controller outputs alarm information in relation to the turn-on state thereof in a simultaneous manner or that a selected one of the first and second AEC signal output devices should be in the turn-on state.

The information acquisition device includes a user interface device for receiving the information of the first and second switching operations in a displayed region. If one of the first and second AEC signal output devices is set in the turn-on state, the controller disables setting of a remaining one of the first and second AEC signal output devices in the turn-on state with the displayed region.

In one preferred embodiment, the information acquisition device further acquires first and second local area information of local areas in the first and second AEC signal output devices. Furthermore, a first judging device receives body part information of a body part of the object to be imaged, checks relevancy of each of the first and second local area information to the body part information, and selects the first or second local area information with higher relevancy to the body part information, to judge one of the first and second AEC signal output devices corresponding thereto by carrying out a first judgment.

If the first and second AEC signal output devices are in the turn-on state simultaneously, the first judging device carries out the first judgment. According to a result of the first judgment, the controller selects one of the first and second AEC signal output devices of which a local area is more relevant to the body part.

Furthermore, a second judging device checks whether one state of the first and second AEC signal output devices among the turn-on and turn-off states is appropriate according to a result of the first judgment by carrying out a second judgment.

If inappropriateness is judged in the state among the turn-on and turn-off states of the first and second AEC signal output devices by the second judgment, the controller changes over the state to an appropriate state according to a result of the second judgment by transmitting a command signal.

If inappropriateness is judged in the state of the first and second AEC signal output devices by the second judgment, the controller outputs alarm information that the state is inappropriate or that the state should be changed over to an appropriate state.

The radiation source driver includes a first control interface, connected to the first AEC signal output device, for receiving the first AEC signal. A second control interface is connected to the second AEC signal output device, for receiving the second AEC signal. The information acquisition device checks the connected state of the first AEC signal output device to the first control interface and of the second AEC signal output device to the second control interface. If the first AEC signal output device is connected to the first control interface and also the second AEC signal output device is connected to the second control interface, the controller selects one of the first and second AEC signal output devices.

The controller is incorporated in the radiation source driver.

In still another preferred embodiment, the controller is external to the radiation source driver and the radiographic imaging apparatus.

The radiographic imaging apparatus has an electronic cassette having a portable housing for containing the radiographic imaging panel.

Also, a radiographic imaging system is provided, and includes a radiation generating apparatus, having a radiation source and a radiation source driver for driving the radiation source, for applying radiation to an object. A radiographic imaging apparatus has a radiographic imaging panel, for detecting the radiation transmitted through the object, to create a radiation image. A first AEC signal output device is external to the radiographic imaging apparatus, for detecting a dose of the radiation transmitted through the object, to output a first AEC signal for automatic exposure control. A second AEC signal output device is incorporated in the radiographic imaging apparatus, for detecting a dose of the radiation transmitted through the object, to output a second AEC signal for automatic exposure control. An exposure control unit is disposed with the radiation source driver, for shutting off application of the radiation from the radiation source according to the first or second AEC signal from the first or second AEC signal output device. An information acquisition device acquires at least one of first information of a first switching operation as to whether the first AEC signal output device should be used, second information of a second switching operation as to whether the second AEC signal output device should be used, and information of a connected state as to whether the first and second AEC signal output devices are connected to the radiation source driver. A controller prevents failure of simultaneous inputting of the first and second AEC signals to the exposure control unit according to the information acquired by the information acquisition device.

Consequently, safety in the function can be maintained even in use of plural AEC signal output devices, because a controller in a regulating unit checks an error of simultaneous inputting of the first and second detection signals to the exposure control unit.

BRIEF DESCRIPTION OF THE DRAWINGS

The above objects and advantages of the present invention will become more apparent from the following detailed description when read in connection with the accompanying drawings, in which:

FIG. 3A is an explanatory view in a front elevation illustrating an AEC setting window;

FIG. 3B is a table illustrating an AEC setting information;

FIG. 5 is a block diagram schematically illustrating circuit elements including a selector;

FIG. 14 is an explanatory view in a front elevation illustrating an AEC setting window for selecting one of the ionization chamber device and the electronic cassette for AEC;

DETAILED DESCRIPTION OF THE PREFERRED EMBODIMENT(S) OF THE PRESENT INVENTION

Figure 1:
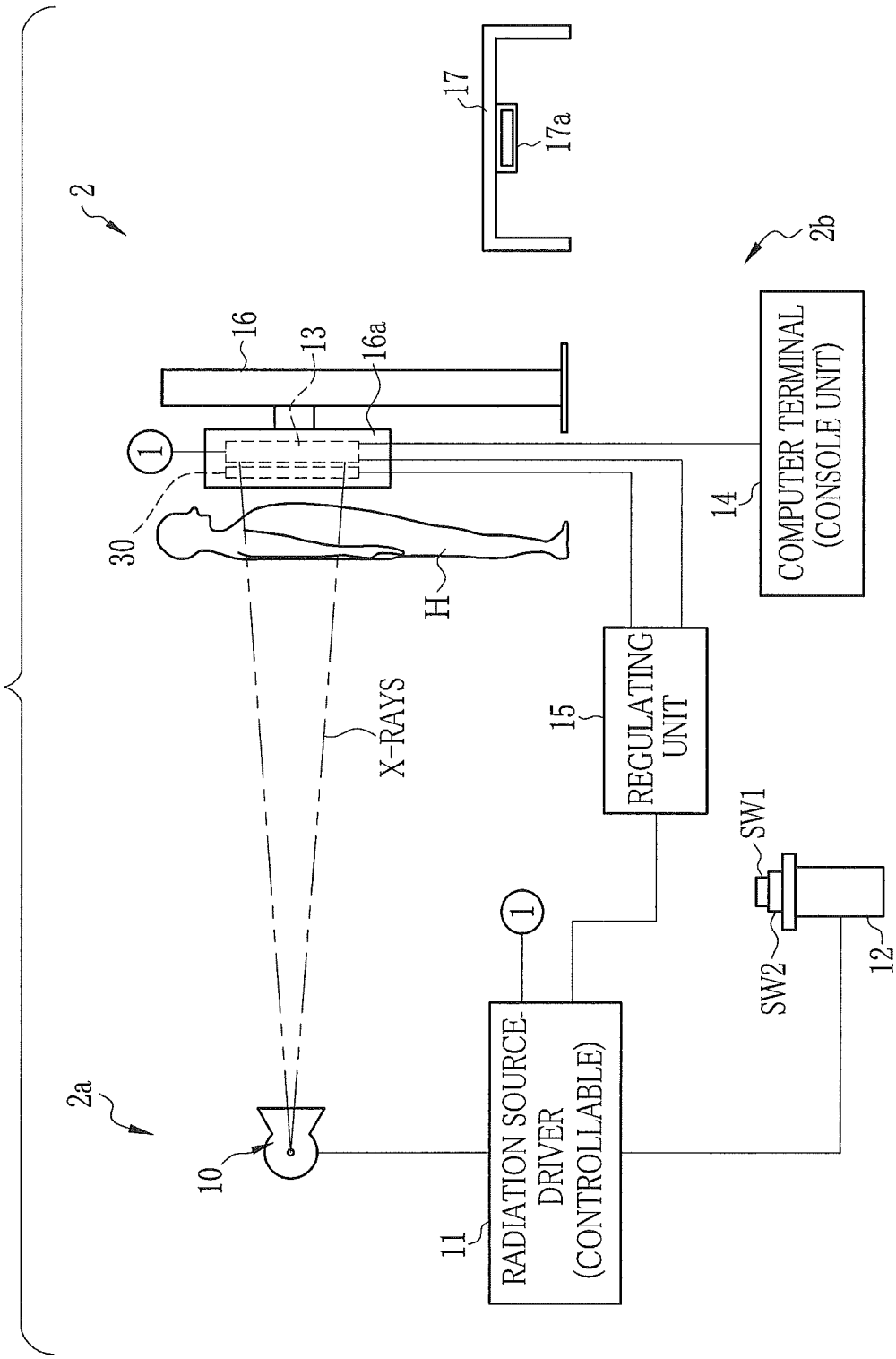
FIG. 1 is an explanatory view in a block diagram schematically illustrating an X-ray imaging system.
Figure 2:
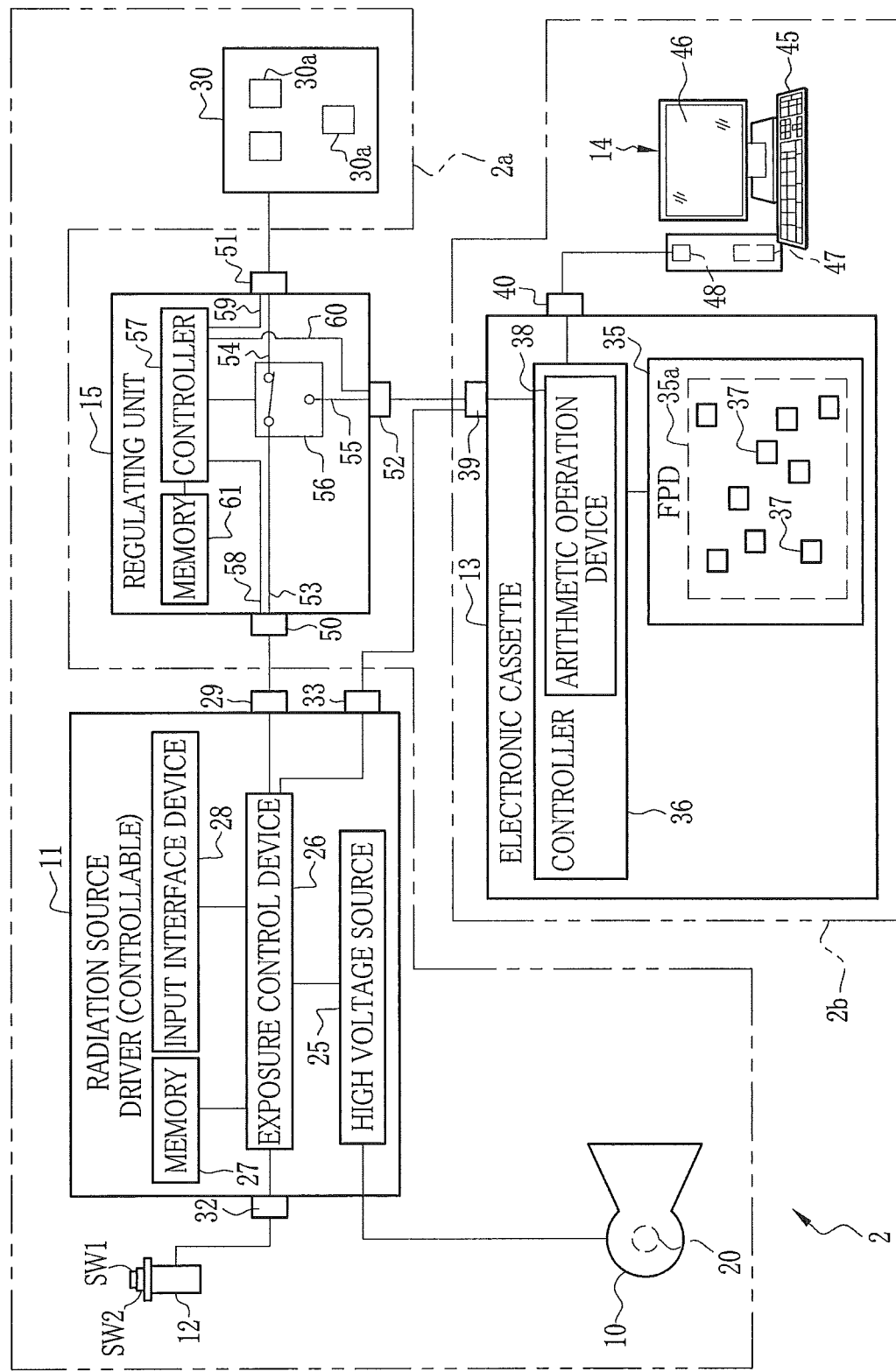
FIG. 2 is a block diagram schematically illustrating the X-ray imaging system.

In FIGS. 1 and 2, an X-ray imaging system 2 as a radiographic imaging system is illustrated, and includes an X-ray source 10 as a radiation source, a (controllable) radiation source driver 11, a source switch 12, an electronic cassette 13 or a radiographic imaging unit, a computer terminal 14 (console unit), a regulating unit 15 or failure prevention unit, a floor stand 16 with an imaging station, and an imaging table 17 with an imaging station. The radiation source driver 11 controls the X-ray source 10. The source switch 12 is operable for starting warmup of the X-ray source 10 and starting irradiation of X-rays in the X-ray source 10. The electronic cassette 13 detects X-rays transmitted through the object H (patient) and outputs an X-ray image. The computer terminal 14 controls operation of the electronic cassette 13 and processes the X-ray image. The floor stand 16 is used for imaging the object H in an erect orientation. The imaging table 17 is used for imaging the object H in a horizontally lying orientation. An X-ray generating apparatus 2a as a radiation generating apparatus is constituted by the X-ray source 10, the radiation source driver 11 and the source switch 12. An X-ray imaging apparatus 2b as a radiographic imaging apparatus is constituted by the electronic cassette 13 and the computer terminal 14. The X-ray generating apparatus 2a is combinable with a film cassette and IP cassette in addition to the electronic cassette 13. Also, a moving mechanism (not shown) is disposed for setting the X-ray source 10 in a desired direction and position. The X-ray source 10 is used in both of the floor stand 16 and the imaging table 17.

The X-ray source 10 includes an X-ray tube 20 and a collimator (not shown) for limiting a region of irradiating X-rays from the X-ray tube 20. The X-ray tube 20 includes a cathode and an anode (target electrode). The cathode has a filament for emitting thermal electron. The anode receives collision of thermal electron from the cathode for emitting X-rays. The collimator includes four plates of lead, and a center opening. The four plates are radiopaque, and arranged in a form of a quadrilateral. The center opening is defined by the four plates for transmitting X-rays. The center opening is changeable for its size. Positions of the plates are shifted to determine a field of irradiation by changing the size of the center opening.

The radiation source driver 11 includes a high voltage source 25 and an exposure control device 26. The high voltage source 25 has a transformer for boosting an input voltage, generates a high voltage as tube voltage, and supplies the X-ray tube 20 with the tube voltage. The exposure control device 26 controls the tube voltage, a tube current and irradiation time of X-rays. The tube voltage determines radiation quality (energy spectrum) of X-rays from the X-ray source 10. The tube current determines an irradiation amount per unit time. The high voltage source 25 is connected to the X-ray source 10 by a high voltage cable.

A memory 27 stores information of the tube voltage, tube current, irradiation time and shut-off threshold in operation of the exposure control device 26, as imaging conditions predetermined for plural objects of interest in a human body. A user interface device 28 or input device, such as a touch panel or the like, is manually operated by an operator such as medical technician, radiologist and the like, to input imaging conditions. Also, the user interface device 28 is operated for selecting one of the film cassette, IP cassette and electronic cassette (with or without an AEC function). A count down timer (not shown) is incorporated in the exposure control device 26 for stopping irradiation of X-rays upon lapse of the predetermined irradiation time.

A target value of the irradiation time for the AEC is set sufficiently large for the purpose of preventing shortage of the dose because of termination of the irradiation before the instruction of terminating the irradiation in the AEC. It is possible to predetermine the maximum irradiation time defined in the X-ray source 10 for public regulation with safety. The exposure control device 26 controls the irradiation of X-rays according to the tube voltage, tube current, irradiation time and the like conditioned in the imaging condition. If it is judged in the AEC that cumulative dose of X-rays has reached an appropriate target dose, the AEC operates to shut off the irradiation of X-rays even if the irradiation time is equal to or shorter than the target irradiation time determined by the radiation source driver 11. In case of no AEC, irradiation time depending upon a body part of an object to be imaged is set. When the built-in count down timer detects lapse of the determined irradiation time, then the exposure control device 26 stops the irradiation.

A control interface 29 (AEC interface) is disposed on the exposure control device 26 for connection with the regulating unit 15. An ionization chamber device 30 is initially connected with the control interface 29 as a first AEC signal output device (detection device), which is discrete from the electronic cassette 13 but incorporated in the X-ray generating apparatus 2a. The ionization chamber device 30 is used for imaging with a film cassette, IP cassette or with an electronic cassette without an AEC function. Holders 16a and 17a are disposed on respectively the floor stand 16 and the imaging table 17. The ionization chamber device 30 is positioned on a front or rear surface of the electronic cassette at any one of the holders 16a and 17a. In FIG. 1, the ionization chamber device 30 is supported on the holder 16a of the floor stand 16. However, positioning of the ionization chamber device 30 is selectively determined for common use between the floor stand 16 and the imaging table 17, as the ionization chamber device 30 can be supported on the holder 17a of the imaging table 17.

First local areas 30a (exposure areas) are disposed in the ionization chamber device 30 in a predetermined position, for example, the right or left lung (chest), the center of the abdomen, and the like. The ionization chamber device 30 outputs a voltage signal at a predetermined interval of sampling according to dose of X-rays transmitted to the first local areas 30a through the object H. The voltage signal is referred to as first dose signal, which corresponds to a first AEC signal.

The first switching operation and the first area selection are carried out by an operator operating the user interface device 28 for conditioning the imaging. In the first switching operation, a turn-on state of the AEC with the ionization chamber device 30 is determined. In the first area selection, a selected one of the first local areas 30a for the AEC is determined. For example, a first AEC setting window 70 as a first AEC setting region of FIGS. 3A and 3B is displayed on a touch panel for manipulation of the operator. The first AEC setting window 70 contains a first switching area 70a and a first area selector 70b. The first switching area 70a is used to select one of a turn-on state of the AEC with the ionization chamber device 30 and a turn-off state of the AEC with the ionization chamber device 30. The first area selector 70b is used to select one of a "chest" (right and left lungs) and "abdomen". The first AEC setting information (operating state information) including information of the first switching operation and the first area selection is output by the control interface 29 to the regulating unit 15 after determination in the first AEC setting window 70.

In the case of a turn-on state in the first switching operation, the ionization chamber device 30 is supplied with power to output a first dose signal of the received dose in a designated one of the first local areas 30a. In the case of a turn-off state in the first switching operation, the ionization chamber device 30 does not operate. No first dose signal is output.

A switch interface 32 is provided on the exposure control device 26. The source switch 12 is connected to the exposure control device 26 by the switch interface 32. An operator manipulates the source switch 12 to start irradiation of X-rays. The buttons SW1 and SW2 are structurally nested in the source switch 12, which is a two-step switch in which the button SW2 is depressible only after depressing the button SW1. When the source switch 12 is depressed halfway to turn on the button SW1, the exposure control device 26 generates a start signal for warmup of the X-ray tube 20. When the source switch 12 is depressed fully to turn on the button SW2, the exposure control device 26 generates a drive signal for instructing irradiation of X-rays in the case of selecting the film cassette or IP cassette, or generates a request signal for checking allowance of starting irradiation of X-rays in the case of selecting the electronic cassette. A port interface 33 or sync signal interface outputs the request signal to the electronic cassette. The electronic cassette generates an enable signal as a response to the request signal. The exposure control device 26, upon receiving the enable signal from the port interface 33, generates the drive signal. A start signal for warmup and the drive signal are sent to the high voltage source 25. The high voltage source 25 starts supplying the X-ray tube 20 with power for irradiation upon receiving the drive signal from the exposure control device 26.

The electronic cassette 13 includes an FPD device 35 (flat panel detector device) as radiographic imaging panel, and a controller 36 for controlling the FPD device 35. The FPD device 35 includes a TFT active matrix substrate and plural arrays of pixels arranged thereon for storing charge according to the dose of X-rays transmitted through the object H. As is well-known, each of the pixels includes a photoelectric converter, a capacitor and a TFT as a switching element. The photoelectric converter generates charge (electron-hole pair) upon incidence of visible light. The capacitor stores charge generated by the photoelectric converter. The FPD device 35 reads signal charge stored in the photoelectric converters in each of the pixels for respectively the signal processing circuit through signal lines associated with respectively the arrays of the pixels. The FPD device 35 outputs an X-ray image by conversion into a voltage signal in the signal processing circuit.

The FPD device 35 includes a scintillator for converting X-rays to visible light, and is an indirect conversion type in which the visible light output by the scintillator is converted by pixels photoelectrically into a signal. Note that the scintillator and the TFT active matrix substrate may be a PSS type (penetration side sampling) in which X-rays enter the scintillator before the board, or an ISS type (irradiation side sampling) in which X-rays enter the board before the scintillator. Also, the scintillator may be omitted. An FPD device can be a direct conversion type in which X-rays are converted into electric charge by a conversion layer, for example, amorphous selenium layer, without a scintillator.

The controller 36 drives the TFT by use of the scan lines associated with the arrays of the pixels. The FPD device 35 is driven by the controller 36 to carry out storing, reading, and resetting. In the storing, the FPD device 35 stores signal charge for pixels according to dose of X-rays. In the reading, the FPD device 35 reads the stored signal charge from the pixels. In the resetting, the FPD device 35 removes the dark current charge created in the pixels. Also, the controller 36 processes image data of X-ray images from the FPD device 35 upon the reading in the image processing of such functions as offset correction, sensitivity correction, defect correction, and the like.

Dose sensors 37 detect dose of X-rays to an imaging area 35a of the FPD device 35 having the pixels. An arithmetic operation device 38 in the controller 36 is supplied with a second dose signal (second AEC signal) output by the dose sensors 37. The dose sensors 37 are arranged regularly in the imaging area 35a without local unevenness in the imaging area 35a.

The dose sensors 37 are constituted by part of the pixels. The particular pixels as the dose sensors 37 are ready to acquire a second dose signal according to the generated charge even while the pixels for the imaging are in the course of the storing. An example of the dose sensors 37 is pixels in which a source and a drain of TFTs are short-circuited to one another. Another example of the dose sensors 37 is pixels in which a photoelectric conversion section is directly connected to a signal line without a TFT, for flow of the generated charge to a signal processing circuit irrespective of turning on and off of a TFT. A still another example of the dose sensors 37 is pixels of which a TFT is driven discretely from the TFTs for the pixels of the imaging.

The arithmetic operation device 38 starts sampling the second dose signal when the FPD device 35 changes over from a standby mode of the repeated resetting to an imaging mode for starting the storing. At each time that the second dose signal is sampled, the arithmetic operation device 38 arithmetically determines an average (maximum, mode value, sum or the like) of the second dose signal from the dose sensors 37 positioned in a second local area according to the body part.

The arithmetic operation device 38 calibrates the second dose signal to a level of the first dose signal output by the ionization chamber device 30. Specifically, the arithmetic operation device 38 multiplies the second dose signal by a coefficient which is according to output levels of the first and second dose signals in irradiation of X-rays in the absence of the object H. For example, let 1 be the output level of the first dose signal in the absence of the object H. Let 10 be the output level of the second dose signal in the absence of the object H. The second dose signal is multiplied by 0.1. There is a port interface 39 or radiation signal interface through which the second dose signal after the calibration is output to the radiation source driver 11. In an embodiment, a second AEC signal output device is constituted by the controller 36 having the dose sensors 37 and the arithmetic operation device 38. Note that, in the case of no AEC by use of the dose sensors 37, the arithmetic operation device 38 does not operate. No second dose signal is output. It is possible arithmetically to determine a coefficient for multiplication of the second dose signal according to such parameters as sensitivity of the ionization chamber device 30 and the dose sensors 37 to X-rays, distances between the X-ray source 10 and the ionization chamber device 30 and between the X-ray source 10 and the dose sensors 37 (the imaging area 35a of the FPD device 35).

The port interface 39 is connected with the port interface 33 of the radiation source driver 11 by a signal cable. The port interface 39 receives a request signal from the port interface 33, and inputs the same to the controller 36. In response to the request signal, the controller 36 changes over the FPD device 35 from the resetting to the storing, and from standby mode to the imaging mode. Also the port interface 39 outputs an enable signal to the port interface 33.

A communication interface 40 is on-line with the computer terminal 14 (console unit) in a wired manner or wirelessly for communication. The communication interface 40 sends and receives information including image data of X-ray images output by the FPD device 35 and an imaging condition determined by the computer terminal 14.

A portable housing of a box shape with a small thickness contains the FPD device 35 and the controller 36. In addition to the FPD device 35, the housing contains a battery (secondary cell) and an antenna. The battery supplies elements of the electronic cassette 13 with power at a predetermined voltage. The antenna wirelessly sends such data to the computer terminal 14 (console unit) as image data of X-ray images and the like.

The housing has a size according to the International Standards ISO 4090:2001 in a manner near to a film cassette and IP cassette. The electronic cassette 13 is removably set in each of the holders 16a and 17a of the floor stand 16 and the imaging table 17 of a conventional form for the film cassette and IP cassette to oppose the imaging area 35a of the FPD device 35 to the X-ray source 10. According to one of the floor stand and the imaging table for use, the X-ray source 10 is moved by a source moving mechanism to set the ionization chamber device 30 in the selected one of the floor stand and the imaging table. Note that the electronic cassette 13 can be used discretely in a state placed on a table where the body H of the patient lies, or a state manually held by the patient.

There is a user interface device 45 or input device which an operator manipulates for inputs, for example, a keyboard. The computer terminal 14 (console unit) controls the electronic cassette 13 according to the inputs. In the computer terminal 14, a display panel 46 displays X-ray images sent from the electronic cassette 13 by the communication interface 40. Data of the X-ray images are stored in a storage medium 47 in the computer terminal 14, or other storage devices such as a memory and storage server in connection with the computer terminal 14 by a network.

The computer terminal 14 (console unit) receives a medical request for examination with information of attributes, such as sex, age, and body part of the person as object H, and a purpose of imaging. The computer terminal 14 drives the display panel 46 to display the medical request. Various methods are available for inputting the medical request. For example, an external system for managing case information and examination information can input the medical request, for example, HIS (hospital information system) and RIS (radiology information system). Also, an operator may manually input the medical request. Examples of the body parts include a head, chest, abdomen, hands, fingers and the like. Also, information of imaging directions can be added to the body parts, such as front direction, lateral direction, diagonal direction, PA (posteroanterior direction) and AP (anteroposterior direction). An operator views various data in the medical request for examination on the display panel 46, and manipulates the user interface device 45 to input an imaging condition by referring to the items on the display panel 46.

Various imaging conditions are stored in the computer terminal 14 (console unit) for respectively body parts. Information of the imaging conditions includes data of a tube voltage, tube current and the like. The storage medium 47 stores the imaging conditions. According to a body part of which an operator designates by use of the user interface device 45, one of the imaging conditions is read from the storage medium 47. A communication interface 48 is disposed so that the acquired imaging condition is sent through the communication interface 48 to the electronic cassette 13. For the radiation source driver 11, the operator refers to the imaging condition from the computer terminal 14 and manually inputs a similar imaging condition.

Figures 4A, 4B:
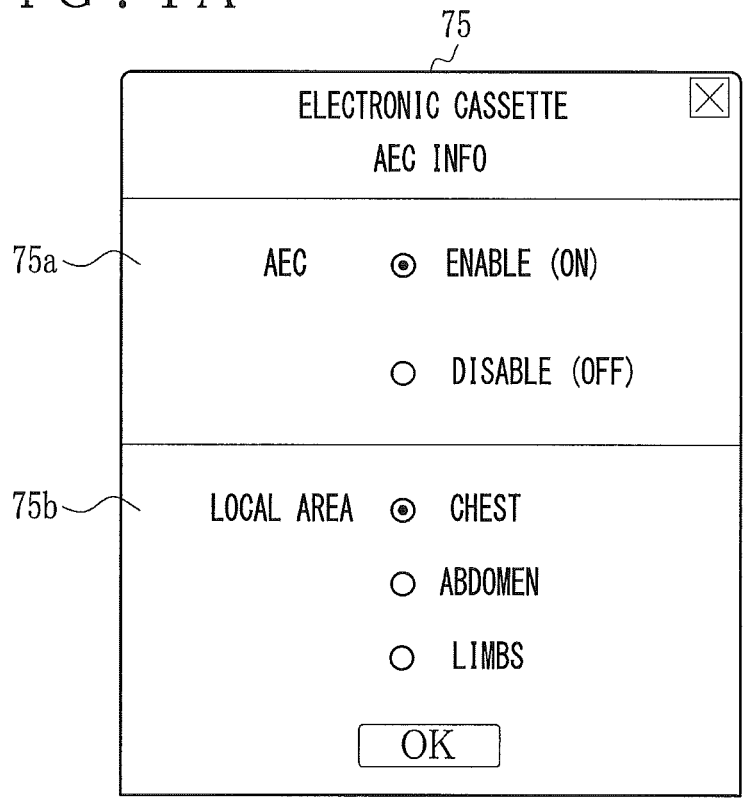
FIGS. 4A and 4B are an explanatory view and a table illustrating an AEC setting window and an AEC setting information.

A second switching operation for the AEC by switching on or off of the dose sensors 37 and second area selection of the dose sensors 37 in the AEC are carried out by the manipulation of the user interface device 45 with an operator at the time of conditioning the imaging. In FIGS. 4A and 4B, a second AEC setting window 75 as a second AEC setting region is disposed in the display panel 46 and is operated manually by an operator. The second AEC setting window 75 has a second switching area 75a and a second area selector 75b. The second switching area 75a is for selection between a "turn-on state" of the AEC by use of the dose sensors 37 and a "turn-off state" of the AEC without use of the dose sensors 37 in a manner similar to the first AEC setting window 70. The second area selector 75b is for selective setting among plural objects such as chest, abdomen and limbs as a second local area. The second AEC setting information (operating state information) containing the second switching operation and second area selection designated with the second AEC setting window 75 is output to the electronic cassette 13 by the communication interface 40 together with information of the imaging condition. Also, the port interface 39 of the electronic cassette 13 outputs the second AEC setting information to the regulating unit 15.

The regulating unit 15 inhibits simultaneous inputs of a first dose signal from the ionization chamber device 30 and a second dose signal from the dose sensors 37 and the controller 36 to the exposure control device 26 of the radiation source driver 11. Note that the "simultaneous" state in the terminology of the present specification includes not only a condition of the start of an input of the first dose signal completely at the same time as an input of the second dose signal and an end of the input of the first dose signal completely at the same time as the input of the second dose signal, but also a condition in which a period of the input of the first dose signal is at least partially the same as a period of the input of the second dose signal. The regulating unit 15 includes a first signal interface 50, a second signal interface 51 and a third signal interface 52. The first signal interface 50 receives the first AEC setting information (operating state information) from the control interface 29, and sends the first dose signal to the control interface 29. The second signal interface 51 receives the first dose signal from the ionization chamber device 30. The third signal interface 52 receives the second AEC setting information and the second dose signal from the port interface 39.

A selector 56 is associated with the signal interfaces 50, 51 and 52. First, second and third signal paths 53, 54 and 55 are selectively connected with the signal interfaces 50-52 by the selector 56.

The regulating unit 15 includes a controller (prevention controller) 57, a fourth signal path 58, a fifth signal path 59 and a sixth signal path 60. The fourth signal path 58 (information acquisition device) connects the first signal interface 50 to the controller 57. The fifth signal path 59 connects the second signal interface 51 to the controller 57. The sixth signal path 60 (information acquisition device) connects the third signal interface 52 to the controller 57. The controller 57 acquires the first AEC setting information (operating state information) through the control interface 29, the signal cable, the first signal interface 50 and the fourth signal path 58, and transmits the first AEC setting information to the ionization chamber device 30 through the fifth signal path 59 and the second signal interface 51. Also, the controller 57 acquires the second AEC setting information through the communication interface 48, the communication interface 40, the port interface 39, the signal cable, the third signal interface 52 and the sixth signal path 60. In short, the first and third signal interfaces 50 and 52 constitute an information acquisition device for setting information. In FIG. 5, a memory 61 stores an operation table 65. The controller 57 drives the selector 56 according to the operation table 65 and the first and second AEC setting information acquired by use of the first and third signal interfaces 50 and 52.

This being so, the controller 57 is an information acquisition device for acquiring the first and second switching operations included in the first and second first AEC setting information. According to the first and second switching operations, the controller 57 judges the turn-on or turn-off state for each of the ionization chamber device 30 (first AEC signal output device) and a combination of the controller 36 and the dose sensors 37 (second AEC signal output device). The controller 57 prevents the first and second AEC signals from simultaneous entry to the exposure control device 26 according to the result of the judgment. Specifically, the turn-on state is judged from both of the first and second switching operations. Selective inhibition (exclusive control) is carried out to select either one of the ionization chamber device 30 and the controller 36 with the dose sensors 37 as an active AEC signal output device.

In FIG. 5, the operation table 65 contains information of selective positions of the selector 56 in association with combinations of the first and second switching operations in the first and second AEC setting information (operating state information). If the use of the ionization chamber device 30 is designated in the radiation source driver 11 for the AEC (turn-on state in the first switching operation), and if the use of the dose sensors 37 is designated in the computer terminal 14 (console unit) for the AEC (turn-on state in the second switching operation), then information for controlling the selector 56 is the "cassette position". Then the controller 57 sets the selector 56 for connection with the third signal path 55.

If a turn-on state is set in the first switching operation and if a turn-off state is set in the second switching operation, then the selector 56 is on the side of the "ionization chamber position", as the AEC with the ionization chamber device 30 is instructed in the radiation source driver 11 and no AEC with the dose sensors 37 is instructed in the computer terminal 14 (console unit). The selector 56 is shifted to the second signal path 54 by the controller 57. Also, if a turn-off state is set in the first switching operation irrespective of the second switching operation, the selector 56 may be set in any of the two set positions, because no AEC is carried out with the ionization chamber device 30, and because the exposure control device 26 does not check whether cumulative dose of X-rays has reached the target dose even in receiving a dose signal. In the present example, the selector 56 is set on the side of the second signal path 54, namely the "ionization chamber position".

As the selector 56 is shifted to the second signal path 54, the second signal interface 51 is made in series with the first signal interface 50 by the first and second signal paths 53 and 54, to set the ionization chamber device 30 on-line with the control interface 29. A first dose signal can be sent or received between the radiation source driver 11 and the ionization chamber device 30 through the path from the control interface 29 to the ionization chamber device 30. When the selector 56 is shifted to the third signal path 55, the third signal interface 52 is made in series with the first signal interface 50 by the first and third signal paths 53 and 55, to set the port interface 39 on-line with the control interface 29. A second dose signal can be sent or received between the radiation source driver 11 and the electronic cassette 13 through the path from the control interface 29 to the port interface 39.

The exposure control device 26 checks whether the cumulative dose of X-rays to the imaging area 35a has reached the target dose according to the first or second dose signal input to the control interface 29. The exposure control device 26 carries out accumulation of the first or second dose signal, compares the cumulative dose with the predetermined shut-off threshold or target dose, and judges the reach of the dose.

When the exposure control device 26 judges that the cumulative value becomes more than the shut-off threshold to detect the reach of the cumulative dose to the target dose, the exposure control device 26 stops supply of power from the high voltage source 25 to the X-ray tube 20 to shut off irradiation of X-rays. Note that if a level of the dose signal is remarkably low with influence of implant, it is possible to detect abnormality in the exposure control device 26 and stop irradiation of X-rays.

If the electronic cassette is selected, the exposure control device 26 shuts off irradiation of X-rays, and causes the port interface 33 to output a shut-off signal for informing the shut off of the irradiation. The port interface 39 receives the shut-off signal from the port interface 33, and inputs the same to the controller 36. In response, the controller 36 changes over the FPD device 35 from the storing to the reading.

Figure 6:
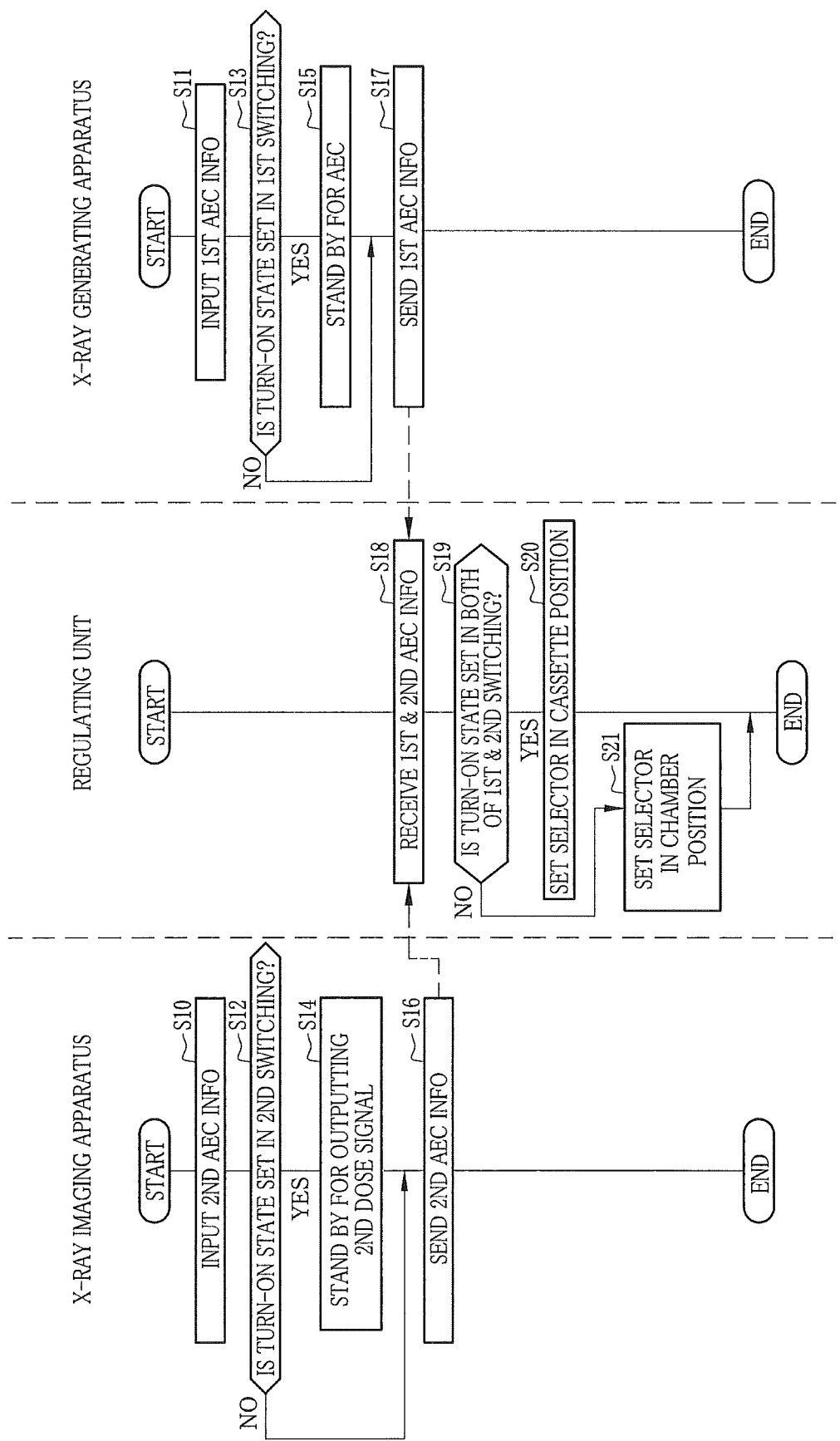
FIG. 6 is a timing chart illustrating operation of error checking.
Figure 7:
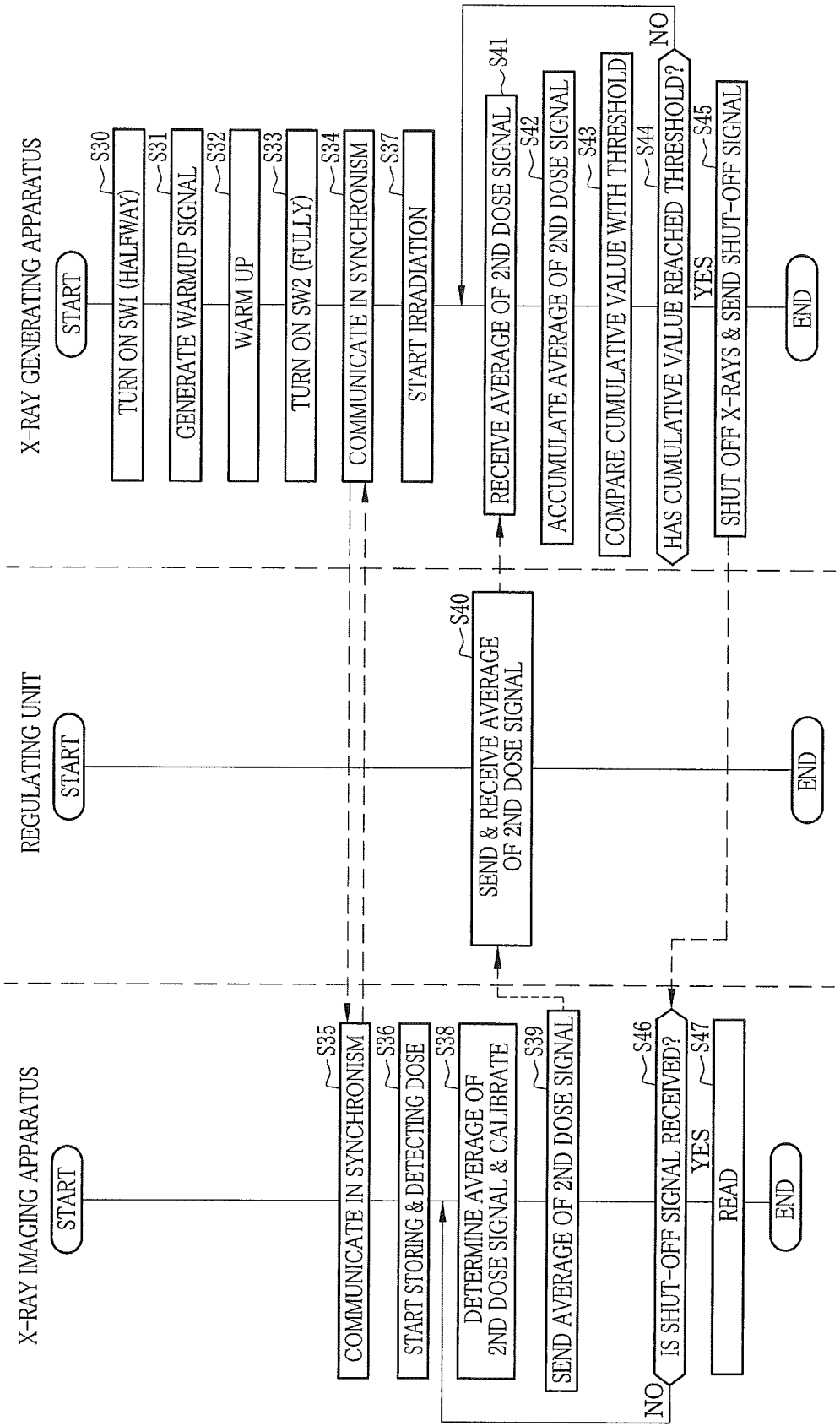
FIG. 7 is a timing chart illustrating X-ray imaging.

The operation of the X-ray imaging system 2 is described now by referring to FIGS. 6 and 7 for one sequence of imaging with X-rays.

At first, the object H is positioned on one of the floor stand 16 and the imaging table 17. A height and horizontal position of the electronic cassette 13 are adjusted to target a region of interest in the object H. Then a height, horizontal position and field size of the X-ray source 10 are adjusted according to the position and a size of the region of interest of the electronic cassette 13. An imaging condition for the radiation source driver 11 and the computer terminal 14 (console unit) is determined. The radiation source driver 11 inputs the first AEC setting information (operating state information) and information of a selected one of the film cassette, IP cassette and electronic cassette. The computer terminal 14 inputs the second AEC setting information. See the steps S10 and S11 in FIG. 6.

For the AEC with the dose sensors 37, a "turn-on state" in the second switching area 75*a* is selected in the second AEC setting window 75. For the AEC with the ionization chamber device 30, a "turn-on state" in the first switching area 70*a* is selected in the first AEC setting window 70. In the case of a turn-on state in the second switching operation (yes in the step S12), the electronic cassette 13 is changed over (S14) and becomes ready for outputting a second dose signal in the port interface 39. In the case of a turn-on state in the first switching operation (yes in the step S13), the radiation source driver 11 is changed over (S15) and becomes ready for the judgment by receiving the dose signal from the control interface 29. In the case of a turn-off state in both of the first and second switching operations (no in the steps S12 and S13), no preparatory operation is carried out.

The first AEC setting information (operating state information) is input by the first signal interface 50 to the controller 57 of the regulating unit 15. The second AEC setting information is input by the third signal interface 52 to the controller 57. See the step S16, S17 and S18.

In normal conditions, a turn-on state is set in both of the first and second switching operations. If no AEC is carried out, a turn-off state is set in the first switching operation, or in both of the first and second switching operations (no in the step S19). However, a turn-on state may be inadvertently set in both of the first and second switching operations by an error of an operator, typically when only one of the first and second switching operations is changed over to the turn-on state. Therefore, the selector 56 is set on the side of the third signal path 55 by the controller 57 in the "cassette position" (S20). Thus, the radiation source driver 11 is made on-line with the electronic cassette 13 by the regulating unit 15. In the case of "no" in the step S19, the selector 56 is set on the side of the second signal path 54 in the "ionization chamber position". The radiation source driver 11 is made on-line with the ionization chamber device 30 by the regulating unit 15 (S21). The operation in the condition of selecting the electronic cassette 13 and setting the selector 56 in the "cassette position" will be hereinafter described.

When the imaging is ready in FIG. 7, the operator depresses the source switch 12 halfway (turns on the switch SW1) in the step S30. The radiation source driver 11 sends a start signal to the high voltage source 25 for warmup in the step S31. The high voltage source 25 starts supplying the X-ray tube 20 with power for its warmup in the step S32.

The operator depresses the source switch 12 halfway and then depresses the source switch 12 fully to turn on the switch SW2 (S33) by manually monitoring time required for the warmup. Then communication is carried out between the radiation source driver 11 and the electronic cassette 13 for transmitting a request signal for starting the irradiation and an enable signal for the irradiation in the steps S34 and S35. In the electronic cassette 13, the operation of the FPD device 35 is changed over from the resetting to the storing. Also, sampling of the dose signal in the arithmetic operation device 38 is started in the step S36.

The enable signal generated by the electronic cassette 13 is input to the radiation source driver 11. Thus, the X-ray tube 20 emits X-rays in the step S37.

When irradiation of X-rays starts, a second dose signal according to a dose of the X-rays is output by the dose sensors 37. The second dose signal is sent to the arithmetic operation device 38. According to the information of a second local area (exposure area) from the computer terminal 14, the arithmetic operation device 38 calculates an average of the dose signal from part of the dose sensors 37 disposed in the second local area. The arithmetic operation device 38 calibrates the average to a level of the first dose signal, before being sent to the regulating unit 15 (S38 and S39).

The calibrated average of the second dose signal received by the regulating unit 15 is sent to the radiation source driver 11 through the third signal path 55, the selector 56 and the first signal path 53 in the steps S40 and S41. The radiation source driver 11 arithmetically determines a cumulative value of plural values of the average of the second dose signal input successively from the regulating unit 15 in the step S42. The cumulative value is compared with the shut-off threshold in the step S43. Those steps are repeated at each time of sampling the second dose signal (no in the step S44).

When the cumulative value increases to reach a shut-off threshold (yes in the step S44), the radiation source driver 11 detects that the cumulative dose of X-rays has reached the target dose. The high voltage source 25 is stopped by the radiation source driver 11 from supplying power to the X-ray tube 20. Irradiation of the X-ray source 10 is shut off. Also, a shut-off signal for the irradiation is output to the electronic cassette 13 (S45).

The shut-off signal from the radiation source driver 11 is input to the electronic cassette 13 (yes in the step S46). The FPD device 35 is changed over from the storing to the reading, and outputs image data of X-ray images in the step S47. After the reading, the FPD device 35 returns to the standby mode for resetting. The image data from the FPD device 35 is processed in image processing in various functions, and sent to the computer terminal 14 for the display panel 46 to display the X-ray images for the purpose of medical diagnosis. Thus, the X-ray imaging of one sequence is terminated.

If a turn-on state is set in the first switching operation and a turn-off state is set in the second switching operation, then the exposure control device 26 carries out the AEC according to the first dose signal from the ionization chamber device 30. If a turn-off state is set in the first switching operation, no AEC is carried out. When the count down timer detects the lapse of irradiation time determined by the user interface device 28, the irradiation of X-rays is shut off.

The selector 56 operates according to the operation table 65 for selection between the second signal path 54 for the first dose signal to the radiation source driver 11 and the third signal path 55 for the second dose signal to the radiation source driver 11. The controller 57 controls the selector 56 unfailingly to select one of the second and third signal paths 54 and 55. Even if the AEC with both of the ionization chamber device 30 and the dose sensors 37 is instructed, failure in the AEC can be prevented, because crosstalk or other errors with the first and second dose signals to the radiation source driver 11 can be prevented.

The regulating unit 15 is constituted basically by the selector 56 and the controller 57. A manufacturing cost of the regulating unit 15 can be considerably lower than structurally modifying the radiation source driver 11 or exchanging the radiation source driver 11 for a type specialized for the electronic cassette 13, as the ionization chamber device 30 can be changeable over to the electronic cassette 13 with a function of the AEC. Among various medical service providers, an obstacle to introduction of the electronic cassette 13 in hospitals can be reduced effectively, so that marketing of the electronic cassette 13 can be enhanced.

Furthermore, it is possible to use the film cassette, IP cassette, or well-known electronic cassette without an AEC function, because the AEC can be carried out with the ionization chamber device 30.

In the first embodiment, the selector 56 is shifted on the side of the "cassette position" when a turn-on state is set in both of the first and second switching operations, so that the AEC with the second dose signal is carried out according to the operation table 65. However, it is possible to set the AEC according to the first dose signal by setting the selector 56 on the side of the "ionization chamber position". However, a turn-on state is often set in the first switching operation in the radiation source driver 11. A turn-on state in the second switching operation is set only upon selecting the electronic cassette 13. If a turn-on state is set in both of the first and second switching operations, it is preferable to give priority to the "cassette position" in the manner of the first embodiment. It is possible to construct the operation table 65 in a rewritable manner by access of the memory 61. Information in the operation table 65, namely priority information, can be manually changed by operation of an operator in the case of a turn-on state in both of the first and second switching operations.

Figure 8:
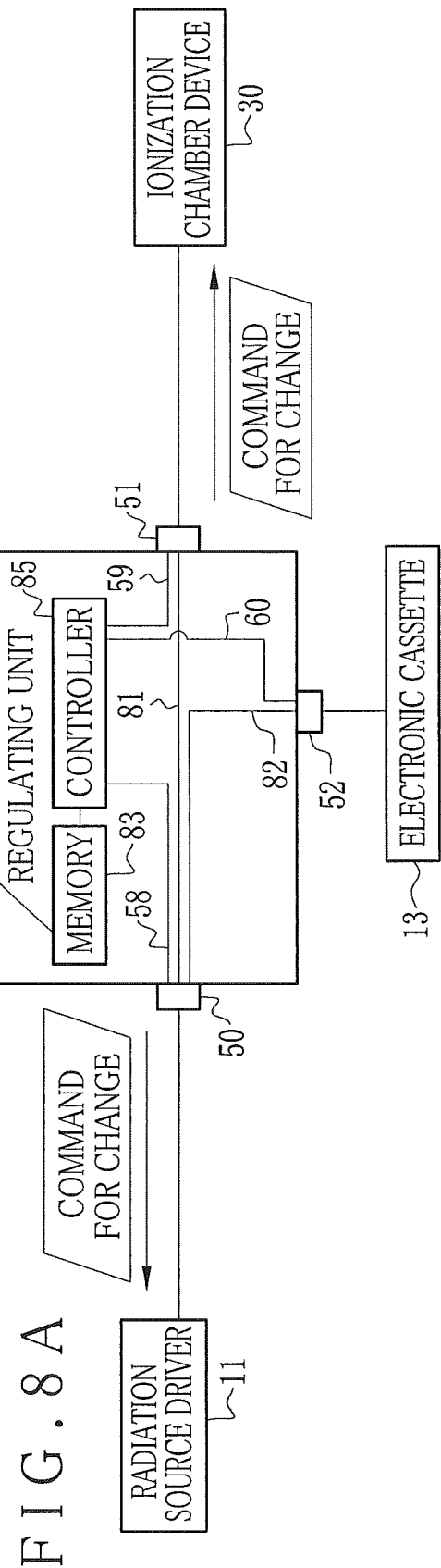
FIGS. 8A and 8B are a block diagram and a table illustrating generation of a command signal from a regulating unit for selecting one of the switching operations.

In the above embodiment, the selector 56 is utilized to use a turn-on state of only one of the first and second switching operations by selecting from the first and second switching operations in the case of a simultaneous turn-on state of the first and second switching operations, as exclusive control or selective inhibition. In FIGS. 8A and 8B, another preferred embodiment for the selective inhibition is illustrated. A regulating unit 80 or failure prevention unit generates a command signal for changing a switch state of only one of the first and second switching operations.

In FIG. 8A, the regulating unit 80 is different from the regulating unit 15 because of the lack of the selector 56. A signal path 81 directly connects the first signal interface 50 with the second signal interface 51 in place of the first and second signal paths 53 and 54. A signal path 82 directly connects the first signal interface 50 with the third signal interface 52 in place of the third signal path 55. A memory 83 stores information of a command table 84 in place of the operation table 65. The command table 84 is combinations of switch states of the first and second switching operations and command signals of changing the switch states of the first and second switching operations. A controller (prevention controller) 85 sends a command signal of the change to various elements according to the command table 84 and the first and second switching operations received through the first and third signal interfaces 50 and 52.

If a turn-on state is set in both of the first and second switching operations, a turn-off state for the "ionization chamber" is read according to the command table 84. The controller 85 sends a command signal to the ionization chamber device 30 for turning off a power source. Then the second dose signal is supplied to the radiation source driver 11 without supply of the first dose signal from the ionization chamber device 30. The AEC can be carried out according to the second dose signal. If a turn-on state is set in the first switching operation and a turn-off state is set in the second switching operation, or if a turn-off state is set in both of the first and second switching operations, no corresponding data is read in the command table 84. No command signal for a change is transmitted. If a turn-off state is set in the first switching operation and a turn-on state is set in the second switching operation, the condition is "a turn-on state in the first switching operation and a turn-off state for the ionization chamber". The controller 85 sends a command signal to the radiation source driver 11 for a change of the first switching operation to a turn-on state, and sends a command signal to the ionization chamber device 30 for turning off the power source. Thus, the AEC can be carried out according to the second dose signal in a manner similar to a condition of a turn-on state in both the first and second switching operations.

According to the first embodiment, if the first switching operation is in the turn-off state, no AEC is carried out irrespective of the second switching operation. However, it is possible in the present embodiment to carry out the AEC according to the second dose signal. When the second switching operation is in the turn-on state and the first switching operation is in the turn-off state, a command signal for a change is sent to the radiation source driver 11 for a turn-on state in the first switching operation, and a command signal is sent to the ionization chamber device 30 for turning off the power source. In the case of a turn-on state in the second switching operation, intention for the AEC is recognized. It is possible to operate according to the intention. Note that in the case of a turn-on state in both of the first and second switching operations, it is possible to send a command signal for a change to the electronic cassette 13 not to output a second dose signal. Furthermore, it is possible to send a command signal to the electronic cassette 13 always to turn off in the second switching operation, so that the AEC is carried out always in the ionization chamber device 30. In short, an apparatus in which turn-on and turn-off states in the switching operation are set by the operator's manipulation may be different from the apparatus for use in the AEC. It is possible to display information of the difference on a touch panel of the radiation source driver 11 or the display panel 46 of the computer terminal 14 (console unit) before starting the imaging or before ending the imaging.

In the above embodiments, the radiation source driver and the regulating unit are separate from the one another. However, it is possible in FIG. 9 to incorporate a regulating unit in a radiation source driver.

Figure 9:
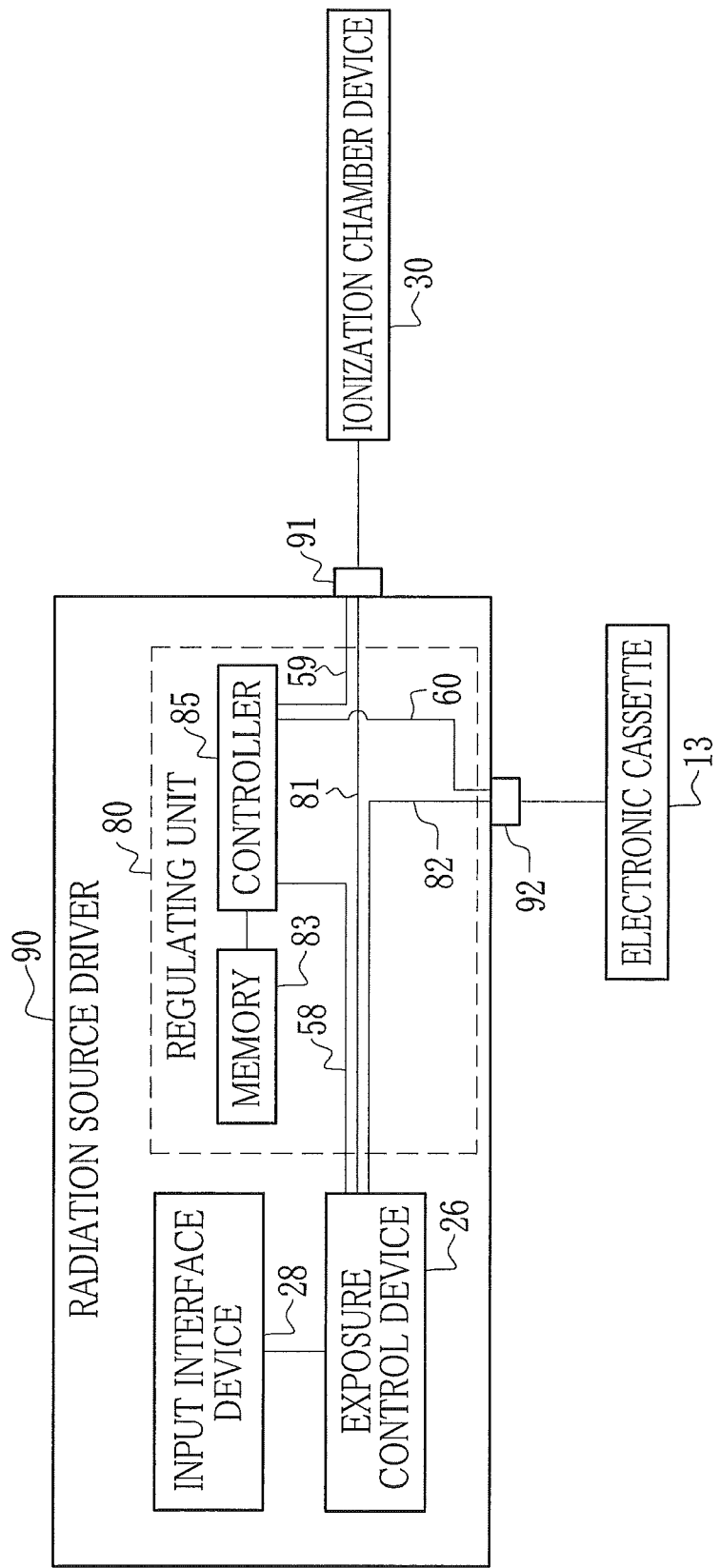
FIG. 9 is a block diagram schematically illustrating another preferred regulating unit incorporated in a radiation source driver.

In FIG. 9, a (controllable) radiation source driver 90 is a combination of the radiation source driver 11 with the regulating unit 80 of the second embodiment. A first control interface 91 (AEC interface) is a unit including sections of the control interface 29 in the radiation source driver 11 and the second signal interface 51 of the regulating unit 80, and adapted for connection of the ionization chamber device 30. A second control interface 92 (AEC interface) is a unit including sections of the port interface 33 in the radiation source driver 11 and the third signal interface 52 of the regulating unit 80, and adapted for connection of the electronic cassette 13. In this structure, the user interface device 28 and the second control interface 92 are combined to constitute an information acquisition device for setting information (operating state information). The selective inhibition (exclusive control) of the second embodiment is repeated herein. Also, it is possible to constitute a single controller by unifying the exposure control device 26 and the controller 85. The regulating unit 15 of the first embodiment can be incorporated in the radiation source driver 11.

Figure 10:
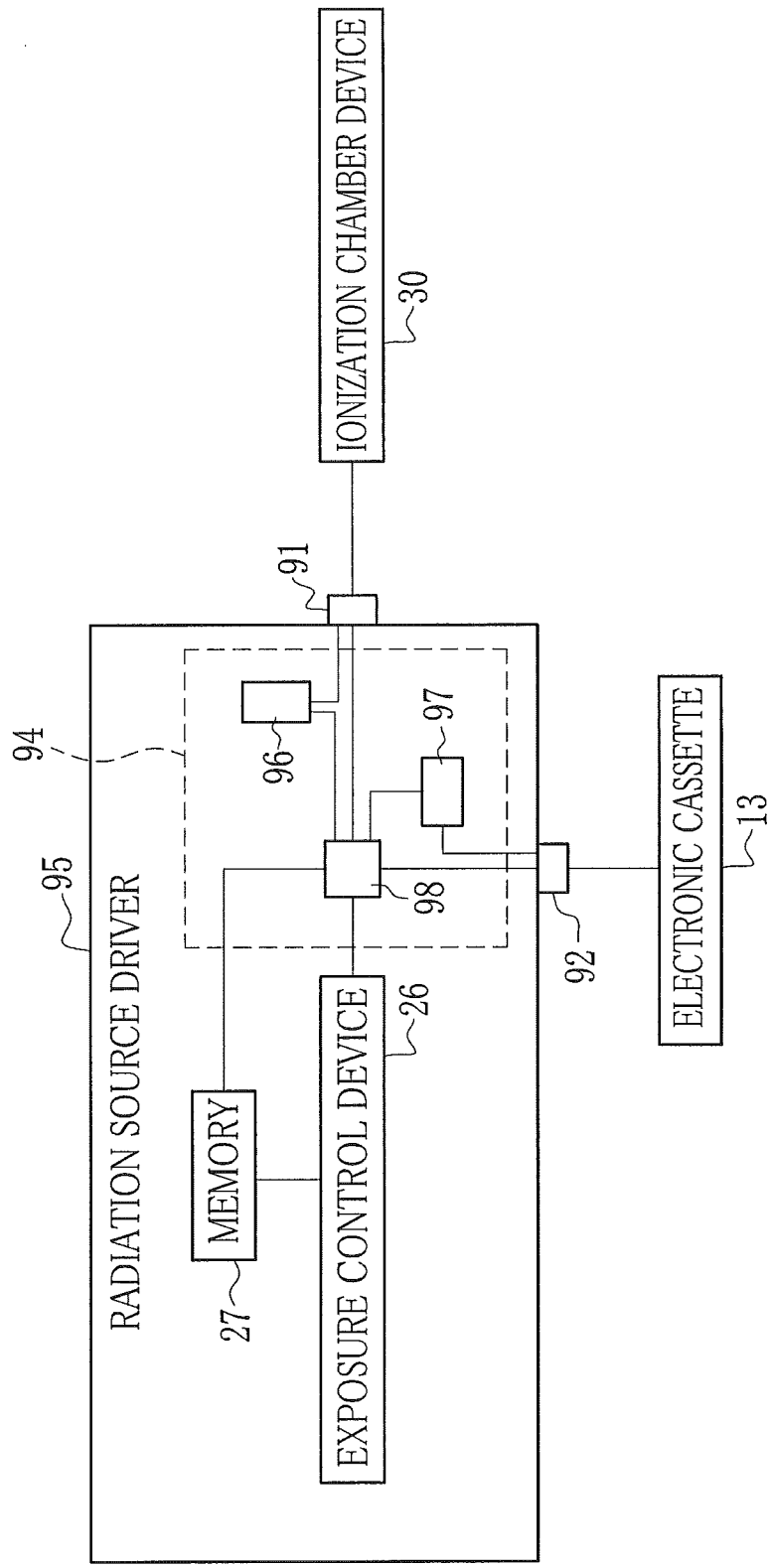
FIG. 10 is a block diagram schematically illustrating another preferred radiation source driver having connection sensors.

A selective inhibition according to another preferred embodiment is described now. In a (controllable) radiation source driver 95 of FIG. 10, the radiation source driver 90 described above is repeated, and has the first control interface 91 for the ionization chamber device 30 and the second control interface 92 for the electronic cassette 13. A regulating unit 94 or failure prevention unit has connection sensors 96 and 97 or detectors (as information acquisition device) incorporated in the radiation source driver 95 for monitoring a connected state of the ionization chamber device 30 and the electronic cassette 13 with the first and second control interfaces 91 and 92. When connection of both of the ionization chamber device 30 and the electronic cassette 13 are detected by the connection sensors 96 and 97, a selector 98 (selection controller) selects one of an input line of the first dose signal from the ionization chamber device 30 and an input line of the second dose signal from the electronic cassette 13, for the purpose of the selective inhibition. An operation table for the selector 98 is stored in the memory 27. Also, the selector 98 may be incorporated in the exposure control device 26. In the present embodiment, an information acquisition device is constituted by the connection sensors 96 and 97 in relation to the connected state. Then the selector 98 selects an active AEC signal output device for use among the ionization chamber device 30 (first AEC signal output device) and the dose sensors 37 and the controller 36 (second AEC signal output device) incorporated in the electronic cassette 13.

Methods of various examples can be used for detecting a connected state between one of the first and second control interfaces 91 and 92 and one of the ionization chamber device 30 and the electronic cassette 13. In a wired connection, a limit switch can be incorporated in a connector which constitutes the first and second control interfaces 91 and 92 for turning on upon coupling with a socket of a signal cable. In a wireless connection, a signal detection can be carried out for detecting transmission and reception of a signal for establishing the wireless connection between one of the first and second control interfaces 91 and 92 and one of the ionization chamber device 30 and the electronic cassette 13.

An alarm function is described now. If a turn-on state is set in both of the first and second switching operations, an alarm signal is generated. Message information of the alarm is notified. Also, message information for an operator to set a turn-off state of either one of the first and second switching operations is generated. Thus, effects similar to those of the above embodiments can be obtained in the alarm function.

Figure 11:
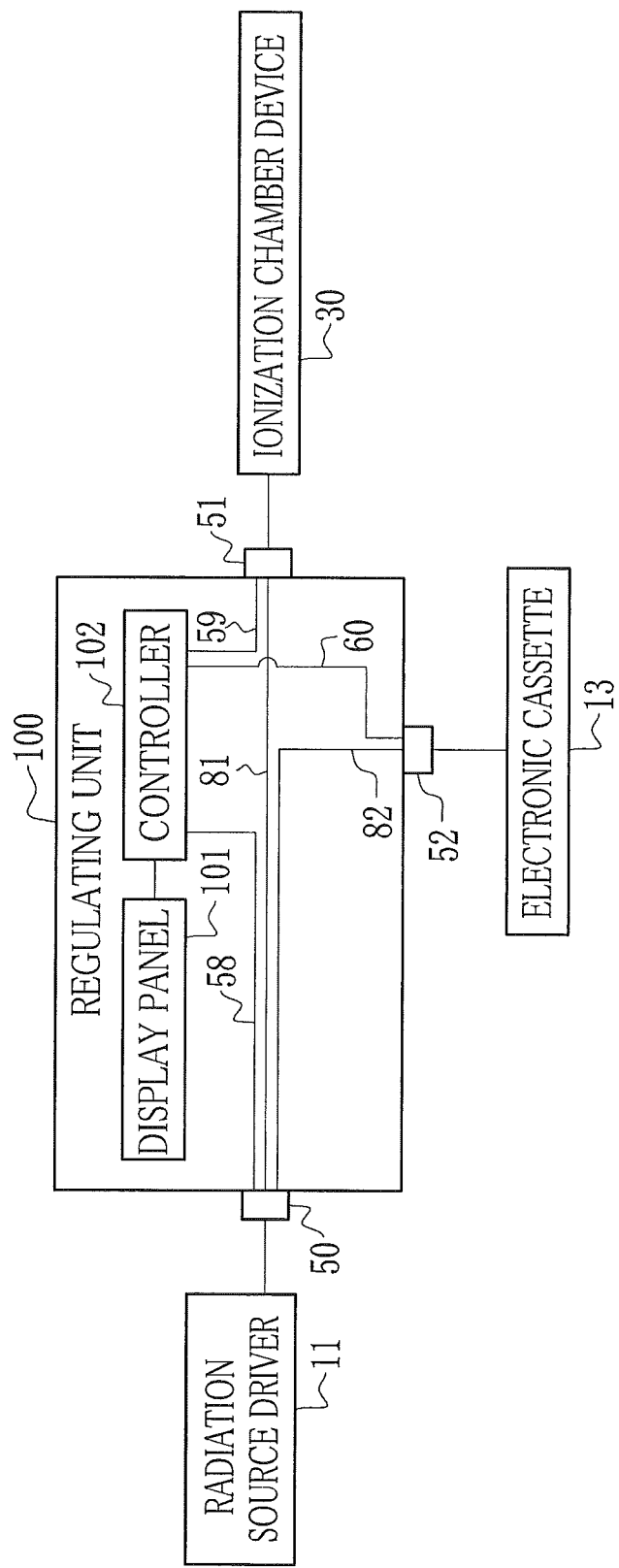
FIG. 11 is a block diagram schematically illustrating another preferred regulating unit with a display panel for displaying an alarm window.

In FIG. 11, a regulating unit 100 or failure prevention unit includes a display panel 101, such as a liquid crystal display panel, in place of the memory 83 in the regulating unit 80. Elements similar to those of the above embodiments are designated with identical reference numerals.

Figure 12:
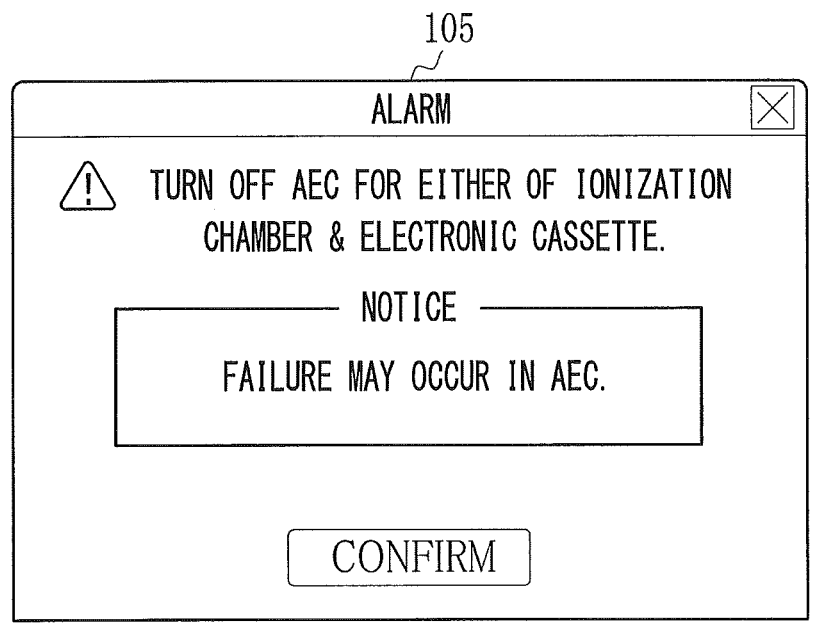
FIG. 12 is an explanatory view in a front elevation illustrating an alarm window for recommending a turn-off state in one of the switching operations.

A controller (prevention controller) 102 acquires the first and second AEC setting information (operating state information) through the first and third signal interfaces 50 and 52 in the manner similar to the above embodiments. In the case of the turn-on state of both of the first and second switching operations, an alarm window 105 as an alarm region of FIG. 12 is displayed on the display panel 101 driven by the controller 102. Also, a sound source is driven to generate beep sound to draw attention of an operator to the alarm. The alarm window 105 displays a message for recommending a turn-off state of at least one of the first and second switching operations. Thus, it is possible to prevent simultaneous use of the AEC with the ionization chamber device 30 and the AEC with the dose sensors 37. Also, it is possible to notify the turn-on state of both of the first and second switching operations. Also, a message for explicitly recommending a turn-off state of one of the first and second switching operations can be displayed to carry out the AEC with the dose sensors 37, for example, "Turn off AEC for ionization chamber". Also, the regulating unit 100 can send an alarm command signal to the radiation source driver 11 and the computer terminal 14 (console unit) in the case of the turn-on state of the first and second switching operations, so that a touch panel of the radiation source driver 11 or the display panel 46 of the computer terminal 14 may display the alarm window 105. To display the alarm message, it is possible to use only at least one of the radiation source driver 11, the computer terminal 14 and the regulating unit 100, or to use all of those.

Figure 13:
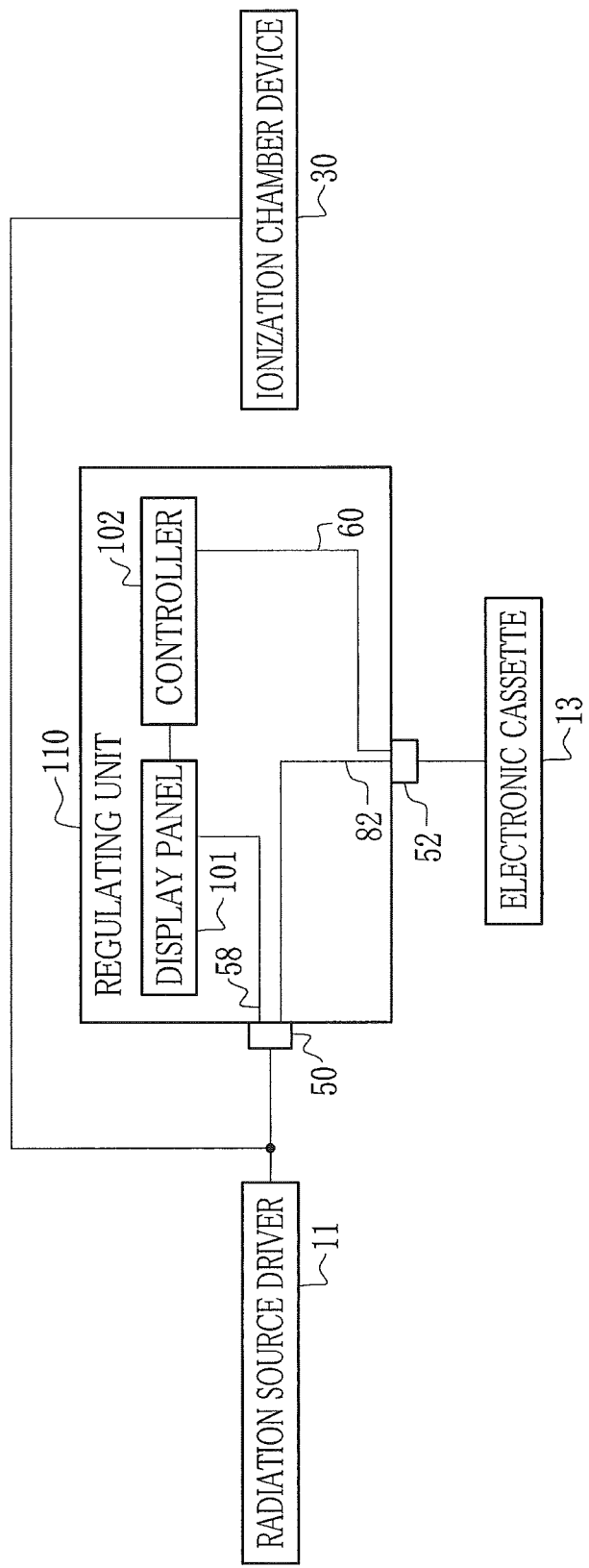
FIG. 13 is a block diagram schematically illustrating an ionization chamber device is made on-line directly with the radiation source driver.

In FIG. 13, another preferred regulating unit 110 or failure prevention unit is illustrated. The ionization chamber device 30 is made on-line with the radiation source driver 11 by signal paths directly irrespective of the regulating unit 110. Among the signal paths between the radiation source driver 11 and the ionization chamber device 30, one for first AEC setting information (operating state information) is branched and connected to the first signal interface 50. This embodiment is advantageous in a simple structure because of the absence of the second signal interface 51 and the signal path 81 of the regulating unit 100.

Another preferred embodiment for regulation with the GUI is described now. If a manufacturer of the X-ray imaging apparatus 2b is different from that of the X-ray generating apparatus 2a, there is no common conditioning between the radiation source driver 11 and the computer terminal 14 (console unit). For this construction, an imaging condition is set in the radiation source driver 11 and the computer terminal 14 discretely from one another in the manner of the first embodiment. Also, the first and second switching operations are carried out in the radiation source driver 11 and the computer terminal 14 discretely. However, it is possible to set an imaging condition in only one of the radiation source driver 11 and the computer terminal 14 in certain systems. Examples of such systems include one in which the computer terminal 14 is communicable with the radiation source driver 11, one in which the computer terminal 14 is included in a unified construction with the radiation source driver 11, and one in which the computer terminal 14 is synchronized with the radiation source driver 11. It is preferable if a manufacturer of the X-ray imaging apparatus 2b is the same as that of the X-ray generating apparatus 2a.

In FIG. 14, an AEC setting window 115 as an AEC setting region is displayed in the display panel 46 of the computer terminal 14, for selecting one of the ionization chamber device 30 and the dose sensors 37 for the purpose of AEC. Specifically, the inputs of the first and second switching operations are received with the AEC setting window 115 to set the AEC. There are two options of the use of the "ionization chamber device" and the use of the "electronic cassette" in the AEC setting window 115. Selection radio buttons 116 are disposed in association with respectively the options. The selection radio buttons 116 are a GUI widget in which a second option cannot be selected after selecting a first option different from the second option. The computer terminal 14 receives information of either one of the first and second switching operations according to the selected one of the selection radio buttons 116 in the AEC setting window 115. The computer terminal 14 acquires the input information of either one of the first and second switching operations, and inhibits setting of one of the ionization chamber device 30 and the dose sensors 37 in the electronic cassette 13 in the turn-on state if a remaining one of the ionization chamber device 30 and the dose sensors 37 is set in the turn-on state. Thus, it is possible to prevent simultaneous designation of the options of the use of the "ionization chamber device" and the use of the "electronic cassette". Also, a drop down list can be used in place of the selection radio buttons 116 for selecting one option among plural options. Furthermore, an unselected option different from the selected option can be deleted or grayed out for easy distinction.

Although the first local area (exposure area) selectable with the radiation source driver 11 is the chest and the abdomen, the second local area selectable with the computer terminal 14 is the chest, abdomen and limbs, so that there is a difference in the options of fields. It is likely that the option "limbs" as second local area may be designated with the computer terminal 14 with non-compatibility of the first local area in the ionization chamber device 30. Should a turn-on state be set in the first switching operation and should a turn-off state be set in the second switching operation for the use of the ionization chamber device 30, failure occurs in the AEC. A preferred embodiment for solving such a problem is hereinafter described.

Figure 15:
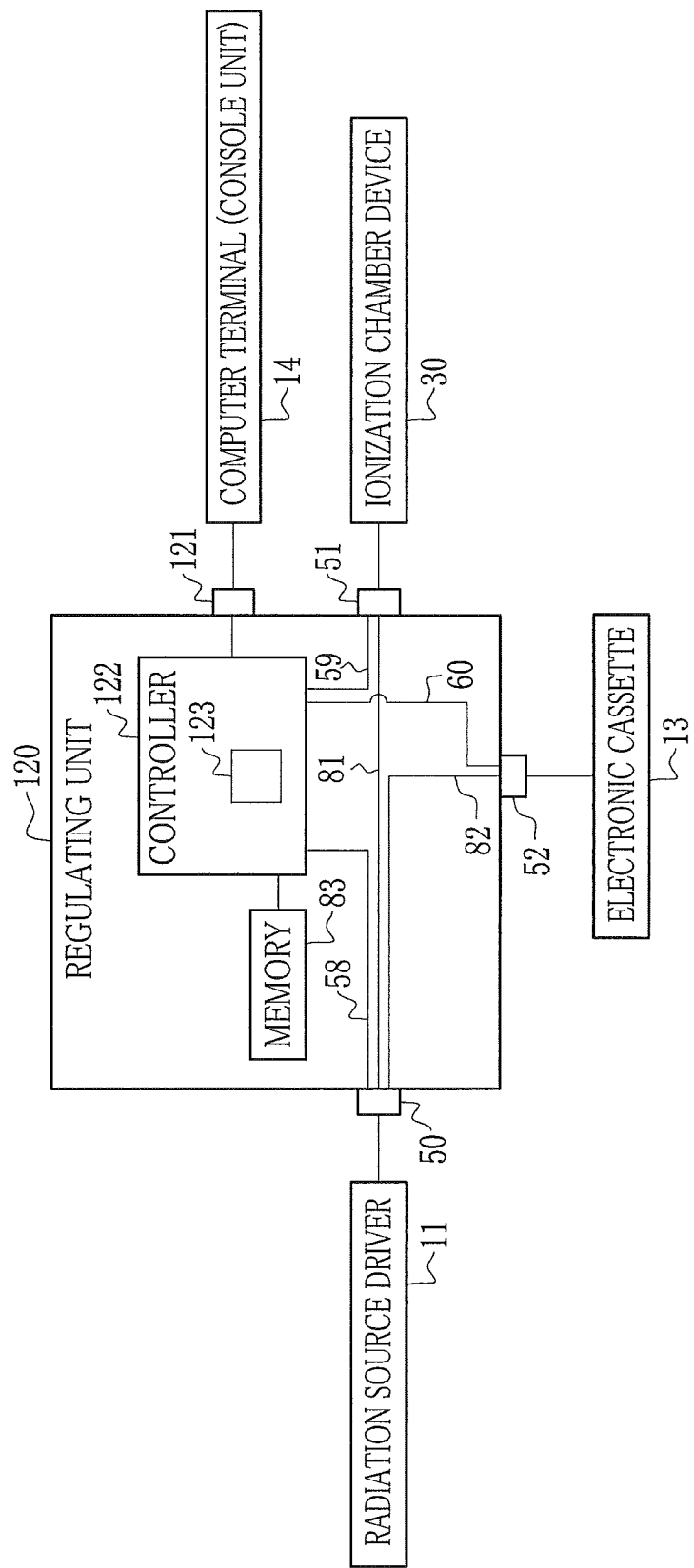
FIG. 15 is a block diagram schematically illustrating another preferred regulating unit with a first judging device.

In FIG. 15, a regulating unit 120 or failure prevention unit is illustrated. The regulating unit 80 is repeated but with a difference in having a port interface 121 or fourth interface, and a first judging device 123. The port interface 121 receives information of a body part of imaging from the computer terminal 14 (console unit). The first judging device 123 is incorporated in a controller (prevention controller) 122.

If a turn-on state is set in both of the first and second switching operations, the first judging device 123 evaluates the information of the body part from the port interface 121 in comparison with the first and second local areas, and selectively detects an appropriate one of the ionization chamber device 30 and the electronic cassette 13 of which relevancy of the local area information to the body part information is higher. This is first area selection. The controller 122 sends a command signal for a change to set a turn-off state in one of the first and second switching operations different from one of which the first judging device 123 has detected the appropriate local area information with higher relevancy (coincidence). For example, let the body part of imaging be "limbs". Let the first local area be "abdomen". Let the second local area be "limbs". The first judging device 123 selectively designates the electronic cassette 13 by judgment of appropriate local area information. The controller 122 sends a command signal for a change to turn off a power source to the ionization chamber device 30.

Figure 16:
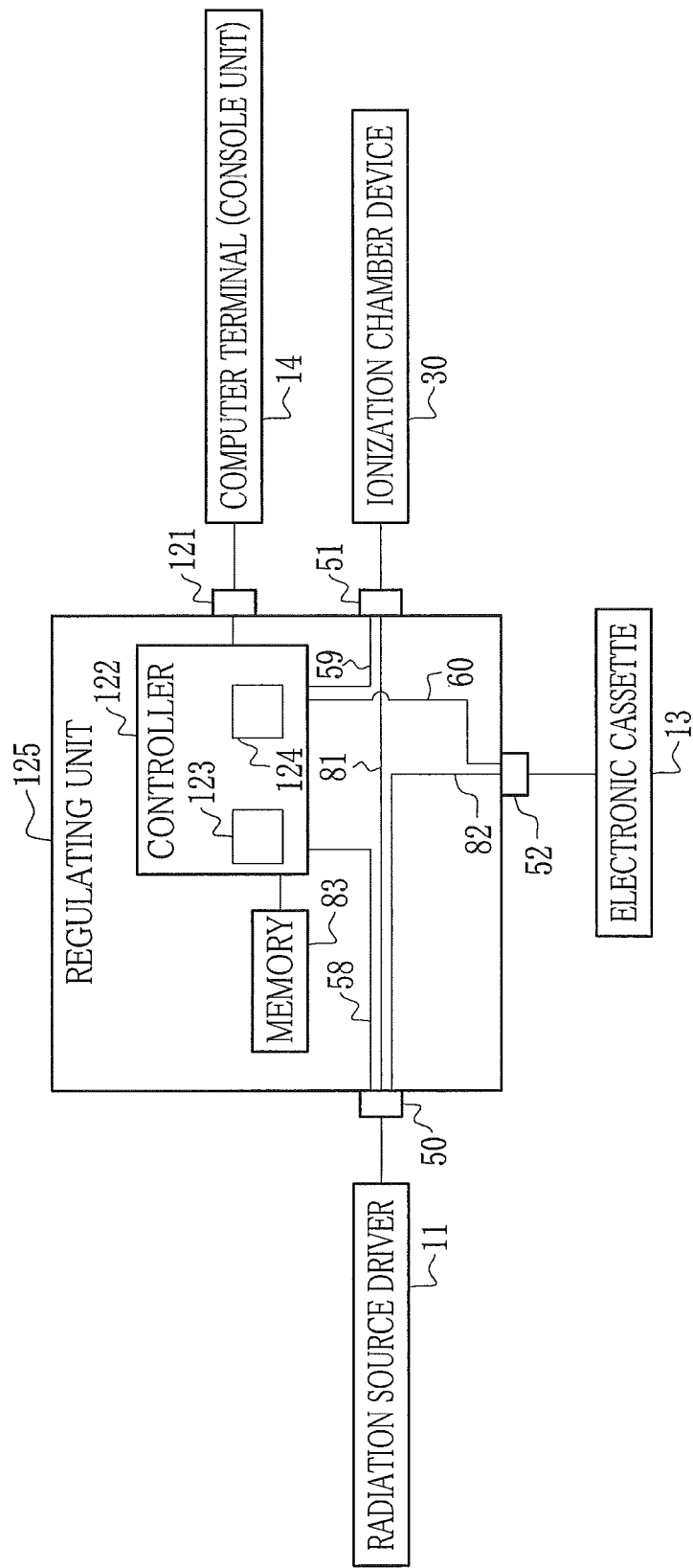
FIG. 16 is a block diagram schematically illustrating another preferred regulating unit with first and second judging devices.

In FIG. 16, another preferred regulating unit 125 or failure prevention unit is illustrated. A second judging device 124 is added in the controller 122. The first judging device 123 operates for the first judgment irrespective of the result of a "turn-on state" in both of the first and second switching operations. The second judging device 124 carries out the second judgment of checking whether the state of the first and second switching operations is suitable or not. For example, if the first judging device 123 has found appropriateness of the electronic cassette 13 for the "limbs" as body part, but if a "turn-on state" is selected in the first switching operation, if a "turn-off state" is selected in the second switching operation, and if the use of the ionization chamber device 30 is set in the AEC, then it is judged that the states of the first and second switching operations are inappropriate. Then the controller 122 sends a command signal for a change to the ionization chamber device 30 to turn off the power source, and sends a command signal for a change to the electronic cassette 13 to output a second dose signal by a turn-on state in the second switching operation.

Figure 17:
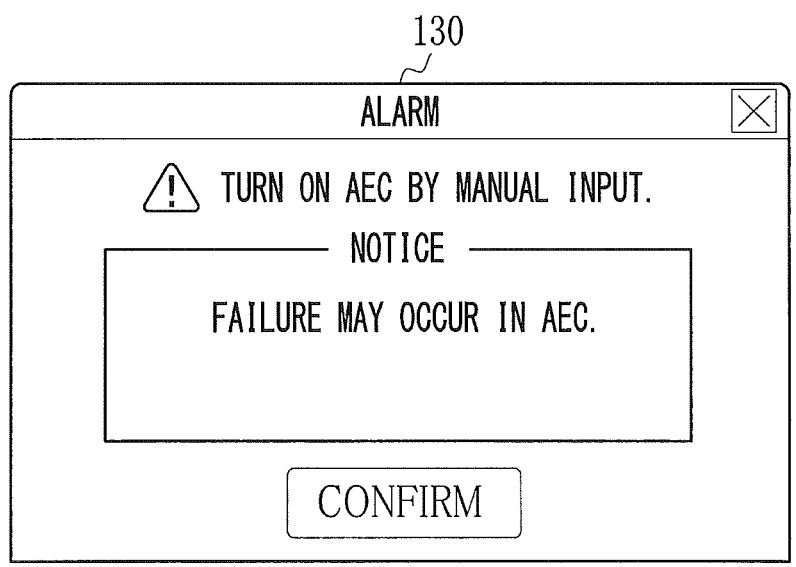
FIG. 17 is an explanatory view in a front elevation illustrating an alarm window for recommending a turn-on state.

Instead of transmitting the command signal for a change, it is possible to notify the operator of inappropriateness of the state of the switching operation, or recommend that the operator should change the state of one of the switching operations of which inappropriateness is judged by the second judging device 124. For example, a body part of the imaging is the "limbs". The electronic cassette 13 is detected appropriate by the first judging device 123. If a turn-on state is set in the first switching operation and if a turn-off state is set in the second switching operation to use the ionization chamber device 30 for the AEC, then an alarm window 130 as an alarm region of FIG. 17 is displayed on the display panel 46 of the computer terminal 14 (console unit) to recommend the use of the dose sensors 37 for the AEC.

In any one of the above embodiments, the radiation source driver checks whether the cumulative dose of X-rays has reached the target dose. However, the ionization chamber device or electronic cassette may be provided with a judgment function in place of the radiation source driver. If it is judged that the cumulative dose has reached the target dose, the ionization chamber device or electronic cassette outputs a shut-off signal to the radiation source driver as an AEC signal (first or second). In response to the shut-off signal, the radiation source driver shuts off irradiation of X-rays from the X-ray source 10. Also, the ionization chamber device or electronic cassette continues outputting an irradiation signal as an AEC signal (first or second) until it is judged that the cumulative dose has reached the target dose. The irradiation signal is terminated upon the reach of the cumulative dose to the target dose. The radiation source driver continues the irradiation of X-rays during reception of the irradiation signal from the ionization chamber device or electronic cassette, and terminates the irradiation from the X-ray source upon termination of the irradiation signal.

If the ionization chamber device does not have a judgment function and if the electronic cassette has a judgment function, the radiation source driver is constructed for receiving a first dose signal (first AEC signal) from the ionization chamber device and a shut-off signal or irradiation signal (second AEC signal) from the electronic cassette in a selectable manner. The radiation source driver is provided with a judgment function according to the first dose signal. At the time of the first switching operation, an operator is notified of recommended selection of one of the first dose signal and the shut-off signal or irradiation signal to be received. Furthermore, it is possible in the manner of the second embodiment to set a mode for receiving the first dose signal in the case of using the ionization chamber device for the AEC and a mode for receiving the shut-off signal or irradiation signal in the case of using the electronic cassette for the AEC. For setting the modes, a command signal for a change can be sent from the regulating unit to the radiation source driver.

In the above embodiments, the storing of the FPD device 35 and irradiation of X-rays are synchronized with one another by communication between the port interfaces 33 and

39 with a request signal and an enable signal. However, it is possible to incorporate a detector in the electronic cassette 13 for detecting a start of irradiation of X-rays, so that the FPD device 35 can be changed over to the storing upon detection of a start of the irradiation with the detector.

In the above embodiments, the irradiation of X-rays is shut off when the cumulative value of the dose signal reaches the shut-off threshold, as the cumulative dose has reached the target dose. However, it is possible to determine estimated time of reach of the cumulative dose of X-rays to the target dose according to cumulative value of the dose signal, and to shut off the irradiation upon the lapse of the determined estimated time.

Also, it is possible to detect dose of X-rays by monitoring a current through a bias line connected with particular pixels, as it is possible to utilize a current according to charge generated with pixels on the bias line for supplying bias voltage in the FPD device. In this structure, the pixels for monitoring the current through the bias lines are dose sensors. Furthermore, the dose can be detected by monitoring a leak current flowing from pixels. In this structure, the pixels for monitoring the leak current are dose sensors. Also, dose sensors can be discretely disposed in an imaging area in a structure different from the pixels for discrete outputs.

In the above embodiments, the computer terminal 14 (console unit) is separate from the electronic cassette 13. However, the electronic cassette 13 may include a section of the computer terminal 14 as a unified component. Also, the radiation source driver 11 can include a section of the computer terminal 14 as one component. Furthermore, an additional control unit for imaging can be connected between the electronic cassette 13 and the computer terminal 14.

Also, it is possible to connect the radiation source driver with the computer terminal (console unit), for the radiation source driver to send the first AEC setting information (operating state information) to the computer terminal, which can carry out the error checking (regulation) described above.

The plural elements in the regulating unit of the invention may be located in one unit or in plural units discrete from one another. The first AEC signal output device (detection device) is not limited to the ionization chamber device, but can be a semiconductor sensor or the like for outputting a signal according to dose of incident X-rays.

Furthermore, two or more of the structures of the above embodiments of the invention may be combined together for the purpose of the failure prevention. Also, it is possible to combine known relevant techniques with any of the above embodiments in the field of failure prevention, error monitoring, alarm, regulation or the like.

In the above embodiment, the radiation is X-rays. However, radiographic imaging of the invention may be a type in which gamma rays or the like is used as radiation.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A regulating unit for a radiographic imaging system including an X-ray radiation generating apparatus for applying X-ray radiation to an object, said X-ray radiation generating apparatus having an X-ray radiation source and an X-ray radiation source driver for driving said X-ray radiation source, a radiographic imaging apparatus for detecting said X-ray radiation transmitted through said object to create a radiation image, said radiographic imaging apparatus having a radiographic imaging panel, a first AEC signal output device for detecting a dose of said X-ray radiation transmitted through said object to output a first AEC signal for automatic exposure control, said first AEC signal output device being external to said radiographic imaging apparatus, a second AEC signal output device for detecting a dose of said X-ray radiation transmitted through said object to output a second AEC signal for automatic exposure control, said second AEC signal output device being incorporated in said radiographic imaging apparatus, and an exposure control unit for shutting off application of said X-ray radiation from said X-ray radiation source according to said first or second AEC signal from said first or second AEC signal output device, said exposure control unit being disposed with said X-ray radiation source driver, said regulating unit comprising:

an information acquisition device for acquiring at least one of first information of a first switching operation as to whether said first AEC signal output device should be used, second information of a second switching operation as to whether said second AEC signal output device should be used, and information of a connected state as to whether said first and second AEC signal output devices are connected to said X-ray radiation source driver; and a controller for preventing failure of simultaneous inputting of said first and second AEC signals to said exposure control unit according to said information acquired by said information acquisition device.

2. A regulating unit as defined in claim 1, wherein said information acquisition device acquires said first information of said first switching operation and said second information of said second switching operation;

said controller sets a turn-on or turn-off state for said first and second AEC signal output devices according to said first and second information of said first and second switching operations.

3. A regulating unit as defined in claim 2, wherein if said first and second AEC signal output devices are in said turn-on state simultaneously, said controller carries out exclusive control of selecting one of said first and second AEC signal output devices.

4. A regulating unit as defined in claim 3, wherein said controller sets said turn-on or turn-off state of one of said first and second switching operations to said turn-off state by transmitting a command signal.

5. A regulating unit as defined in claim 3, further comprising a selector for selectively switching a first signal path for inputting said first AEC signal from said first AEC signal output device to said exposure control unit and a second signal path for inputting said second AEC signal from said second AEC signal output device to said exposure control unit;

wherein said controller enables one of said first and second signal paths by use of said selector.

6. A regulating unit as defined in claim 3, further comprising a memory for storing priority information of a selected one of said first and second AEC signal output devices to which priority is given;

wherein said controller carries out said exclusive control according to said priority information.

7. A regulating unit as defined in claim 6, wherein said priority information is changeable by external operation.

8. A regulating unit as defined in claim 2, wherein if said first and second AEC signal output devices are in said turn-on state simultaneously, said controller outputs alarm information in relation to said turn-on state thereof in a simultaneous manner or that a selected one of said first and second AEC signal output devices should be in said turn-on state.

9. A regulating unit as defined in claim 2, wherein said information acquisition device includes a user interface device for receiving said information of said first and second switching operations in a displayed region; and
   if one of said first and second AEC signal output devices is set in said turn-on state, said controller disables setting of a remaining one of said first and second AEC signal output devices in said turn-on state with said displayed region.

10. A regulating unit as defined in claim 2, wherein said information acquisition device further acquires first and second local area information of local areas in said first and second AEC signal output devices;
   further comprising a first judging device for receiving body part information of a body part of said object to be imaged, checking relevance of each of said first and second local area information to said body part information, and selecting said first or second local area information with higher relevancy to said body part information, to judge one of said first and second AEC signal output devices corresponding thereto by carrying out a first judgement.

11. A regulating unit as defined in claim 10, wherein if said first and second AEC signal output devices are in said turn-on state simultaneously, said first judging device carries out said first judgement; and
   according to a result of said first judgement, said controller selects one of said first and second AEC signal output devices of which a local area is more relevant to said body part.

12. A regulating unit as defined in claim 10, further comprising a second judging device for checking whether one state of said first and second AEC signal output devices among said turn-on and turn-off states is appropriate according to a result of said first judgement by carrying out a second judgement.

13. A regulating unit as defined in claim 12, wherein if inappropriateness is judged in said state among said turn-on and turn-off states of said first and second AEC signal output devices by said second judgement, said controller changes over said state to an appropriate state according to a result of said second judgement by transmitting a command signal.

14. A regulating unit as defined in claim 12, wherein if inappropriateness is judged in said state of said first and second AEC signal output devices by said second judgement, said controller outputs alarm information that said state is inappropriate or that said state should be changed over to an appropriate state.

15. A regulating unit as defined in claim 1, wherein said X-ray radiation source driver includes:
   a first control interface, connected to said first AEC signal output device, for receiving said first AEC signal; and
   a second control interface, connected to said second AEC signal output device, for receiving said second AEC signal;
   wherein said information acquisition device checks said connected state of said first AEC signal output device to said first control interface and of said second AEC signal output device to said second control interface; and
   if said first AEC signal output device is connected to said first control interface and also said second AEC signal output device is connected to said second control interface, said controller selects one of said first and second AEC signal output devices.

16. A regulating unit as defined in claim 1, wherein said controller is incorporated in said X-ray radiation source driver.

17. A regulating unit as defined in claim 1, wherein said controller is external to said X-ray radiation source driver and said radiographic imaging apparatus.

18. A regulating unit as defined in claim 1, wherein said radiographic imaging apparatus has an electronic cassette having a portable housing for containing said radiographic imaging panel.

19. A radiographic imaging system comprising:
   a X-ray radiation generating apparatus for applying X-ray radiation to an object, said X-ray radiation generating apparatus having an X-ray radiation source and a X-ray radiation source driver for driving said X-ray radiation source;
   a radiographic imaging apparatus, for detecting said X-ray radiation transmitted through said object to create a radiation image, said radiographic imaging apparatus having a radiographic imaging panel;
   a first AEC signal output device, for detecting a dose of said X-ray radiation transmitted through said object to output a first AEC signal for automatic exposure control, said first AEC signal output device being external to said radiographic imaging apparatus;
   a second AEC signal output device for detecting a dose of said X-ray radiation transmitted through said object to output a second AEC signal for automatic exposure control, said second AEC signal output device being incorporated in said radiographic imaging apparatus;
   an exposure control unit for shutting off application of said X-ray radiation from said X-ray radiation source according to said first or second AEC signal from said first or second AEC signal output device, said exposure control unit being disposed with said X-ray radiation source driver;
   an information acquisition device for acquiring at least one of first information of a first switching operation as to whether said first AEC signal output device should be used, second information of a second switching operation as to whether said second AEC signal output device should be used, and information of a connected state as to whether said first and second AEC signal output devices are connected to said X-ray radiation source driver; and
   a controller for preventing failure of simultaneous inputting of said first and second AEC signals to said exposure control unit according to said information acquired by said information acquisition device.

* * * * *